(12) United States Patent
Burbank et al.

(10) Patent No.: US 7,488,295 B2
(45) Date of Patent: *Feb. 10, 2009

(54) TISSUE ACQUISITION SYSTEM AND METHOD OF USE

(75) Inventors: Fred Burbank, San Juan Capistrano, CA (US); Paul Lubock, Laguna Niguel, CA (US); Michael L. Jones, Capistrano Beach, CA (US)

(73) Assignee: SenoRx, Inc., Irvine, CA (US)

( * ) Notice: Subject to any disclaimer, the term of this patent is extended or adjusted under 35 U.S.C. 154(b) by 1142 days.

This patent is subject to a terminal disclaimer.

(21) Appl. No.: 09/981,525

(22) Filed: Oct. 16, 2001

(65) Prior Publication Data

US 2002/0111564 A1    Aug. 15, 2002

Related U.S. Application Data

(60) Division of application No. 09/196,125, filed on Nov. 20, 1998, now Pat. No. 6,454,727, which is a continuation-in-part of application No. 09/057,303, filed on Apr. 8, 1998, now Pat. No. 6,331,166.

(51) Int. Cl.
*A61B 10/00* (2006.01)
*A61B 17/32* (2006.01)

(52) U.S. Cl. .................. 600/564; 600/567; 606/167

(58) Field of Classification Search ......... 600/562–568; 606/39, 40, 45, 167, 170, 171
See application file for complete search history.

(56) References Cited

U.S. PATENT DOCUMENTS

| | | | |
|---|---|---|---|
| 2,032,860 A | 3/1936 | Wappler et al. | |
| 3,805,791 A | 4/1974 | Seuberth et al. | |
| 3,844,272 A | 10/1974 | Banko | |
| 3,910,279 A | 10/1975 | Okada et al. | |
| 3,955,578 A | 5/1976 | Chamness et al. | |
| 4,202,338 A | 5/1980 | Bitroff | |
| 4,294,254 A | 10/1981 | Chamness | |
| 4,311,143 A | 1/1982 | Komiya | |

(Continued)

FOREIGN PATENT DOCUMENTS

DE    19528440 A1    8/1995

(Continued)

OTHER PUBLICATIONS

The Loop Electrode: a New Device for US-guided Interstitial Tissue Ablation Using Radio frequency Electrosurgery—An Animal Study, 1996 Blackwell Science Ltd. *Min Incas Ther & Allied Technol*, pp. 5.511-5.516.

(Continued)

*Primary Examiner*—Max Hindenburg
*Assistant Examiner*—Jonathan M Foreman
(74) *Attorney, Agent, or Firm*—Edward J. Lynch

(57) ABSTRACT

A tissue acquisition system includes radio frequency (RF) cutter loops which are extendable out a cannula to cut cylindrical tissue samples from a tissue of interest in a patient. The cannula includes inner and outer cannulae which are mutually rotatable and include cutouts through which the cutting loop can be rotated and longitudinally extended to perform the cuts. The tissue samples are then aspirated proximally through the cannula for collection.

15 Claims, 15 Drawing Sheets

U.S. PATENT DOCUMENTS

| | | | |
|---|---|---|---|
| 4,362,160 A | 12/1982 | Hiltebrandt | 128/303.15 |
| 4,503,855 A | 3/1985 | Maslanka | |
| 4,576,162 A | 3/1986 | McCorkle | |
| 4,638,802 A | 1/1987 | Okada | |
| 4,718,419 A | 1/1988 | Okada | |
| 4,724,836 A | 2/1988 | Okada | |
| 5,007,908 A | 4/1991 | Rydell | |
| 5,024,617 A | 6/1991 | Karpiel | |
| 5,035,696 A | 7/1991 | Rydell | |
| 5,064,424 A | 11/1991 | Bitrolf | 606/46 |
| 5,066,295 A | 11/1991 | Kozak et al. | |
| 5,078,716 A | 1/1992 | Doll | |
| 5,080,660 A | 1/1992 | Buelna | |
| 5,085,659 A | 2/1992 | Rydell | |
| RE33,925 E | 5/1992 | Bales et al. | |
| 5,111,828 A | 5/1992 | Kornberg et al. | |
| 5,133,360 A | 7/1992 | Spears | 128/754 |
| 5,158,561 A | 10/1992 | Rydell et al. | |
| 5,163,938 A | 11/1992 | Kambara et al. | |
| 5,196,007 A | 3/1993 | Ellman et al. | |
| 5,201,732 A | 4/1993 | Parins et al. | |
| 5,201,741 A | 4/1993 | Dulebohn | |
| 5,207,686 A | 5/1993 | Dolgin | |
| 5,224,488 A | 7/1993 | Neuffer | |
| 5,312,400 A | 5/1994 | Bales et al. | |
| 5,318,564 A | 6/1994 | Eggers | |
| 5,323,768 A | 6/1994 | Saito et al. | |
| 5,324,288 A | 6/1994 | Billings et al. | 606/45 |
| 5,335,671 A | 8/1994 | Clement | |
| 5,344,420 A | 9/1994 | Hilal et al. | |
| 5,376,094 A | 12/1994 | Kline | |
| 5,380,321 A | 1/1995 | Yoon | |
| 5,395,312 A | 3/1995 | Desai | |
| 5,415,656 A | 5/1995 | Tihon et al. | 606/46 |
| 5,417,697 A | 5/1995 | Wilk et al. | |
| 5,423,814 A | 6/1995 | Zhu et al. | |
| 5,437,665 A | 8/1995 | Munro | 606/47 |
| 5,441,503 A | 8/1995 | Considine et al. | |
| 5,462,553 A | 10/1995 | Dolgin | |
| 5,477,862 A | 12/1995 | Haga | |
| 5,484,436 A | 1/1996 | Eggers et al. | |
| 5,501,654 A | 3/1996 | Failla et al. | |
| 5,526,822 A | 6/1996 | Burbank et al. | |
| 5,527,331 A | 6/1996 | Kresch et al. | |
| 5,542,948 A | 8/1996 | Weaver et al. | |
| 5,611,803 A | 3/1997 | Heaven et al. | |
| 5,643,282 A | 7/1997 | Kieturakis | |
| 5,649,547 A | 7/1997 | Ritchart et al. | 128/754 |
| 5,665,085 A | 9/1997 | Nardella | |
| 5,674,184 A | 10/1997 | Hassler, Jr. | |
| 5,769,086 A | 6/1998 | Richart et al. | |
| 5,775,333 A | 7/1998 | Burbank et al. | |
| 5,794,626 A | 8/1998 | Kieturakis | 600/567 |
| 5,810,764 A | 9/1998 | Eggers et al. | |
| 5,810,806 A | 9/1998 | Ritchart et al. | |
| 5,882,316 A | 3/1999 | Chu et al. | 600/567 |
| 5,928,164 A | 7/1999 | Burbank et al. | |
| 5,947,964 A * | 9/1999 | Eggers et al. | 606/41 |
| 6,120,462 A | 9/2000 | Hibner et al. | |
| 6,280,450 B1 | 8/2001 | McGuckin, Jr. | |
| 6,454,727 B1 * | 9/2002 | Burbank et al. | 600/567 |
| 6,494,881 B1 * | 12/2002 | Bales et al. | 606/45 |
| 6,514,248 B1 | 2/2003 | Eggers et al. | |
| 6,689,145 B2 | 2/2004 | Lee et al. | |
| 6,712,775 B2 * | 3/2004 | Burbank et al. | 600/567 |

FOREIGN PATENT DOCUMENTS

| | | |
|---|---|---|
| EP | 0472368 A2 | 8/1991 |
| GB | 2311 468 A | 2/1997 |
| WO | PCT/GB94/01536 | 7/1994 |
| WO | PCT/GB94/01537 | 7/1994 |
| WO | 95/02371 | 1/1995 |
| WO | WO 98/43531 | 10/1998 |

OTHER PUBLICATIONS

English translation of German Application DE 195 28 440 A1, published Aug. 2, 1995.

Armstrong J.S. et al., "Differential marking of excision planes in screened breast lesions by organically coloured gelantins [see comments].", *Journal of Clinical Pathology*, (Jul. 1990), 43(7) 604-7, XP000971447 abstract; tables 1 and 2.

* cited by examiner

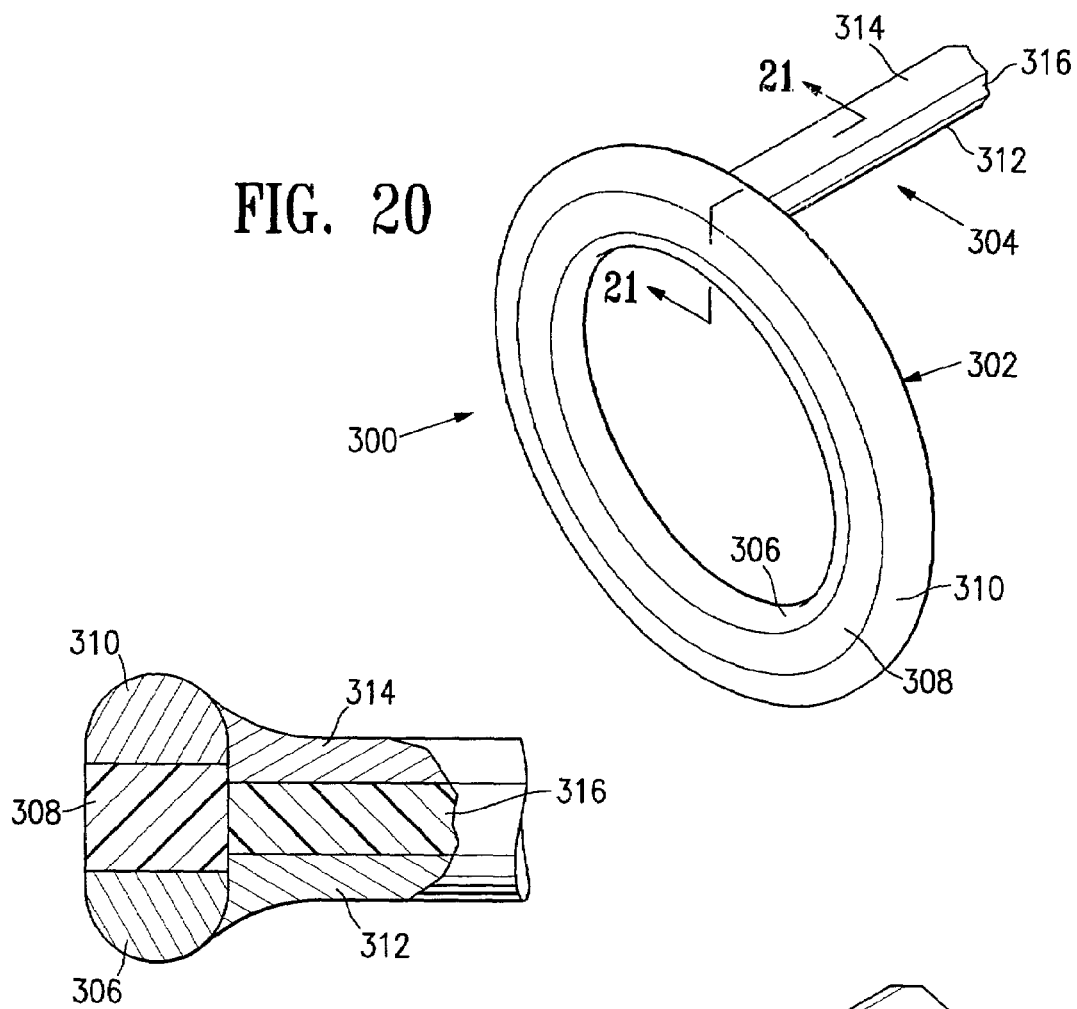
FIG. 20
FIG. 21
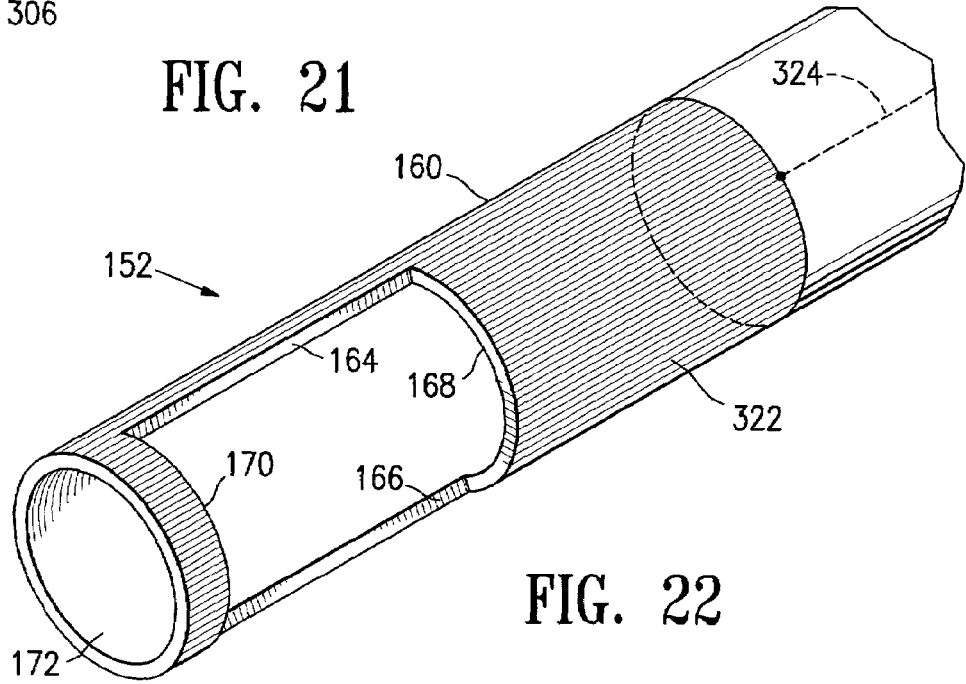
FIG. 22

TISSUE ACQUISITION SYSTEM AND METHOD OF USE

This application is a divisional of patent application Ser. No. 09/196,125, filed Nov. 20, 1998, now U.S. Pat. No. 6,454,727, which is a continuation-in-part of patent application Ser. No. 09/057,303, filed Apr. 8, 1998, now U.S. Pat. No. 6,331,166, which is incorporated by reference herein and which claims benefit to provisional patent application Ser. No. 60/076,973, filed Mar. 3, 1998, entitled "Breast Biopsy System and Method" to Burbank et al, from which priorities are claimed.

BACKGROUND OF THE INVENTION

1. Field of the Invention

The present invention relates to a tissue sampling or removal system, and methods of sampling or removing tissue from a patient, and more particularly to a system and methods for sampling or removing tissue from a patient which maintains the integrity of the tissue sample.

2. Brief Description of the Related Art

It is often desirable and frequently necessary to sample or remove a portion of tissue from humans and other animals, particularly in the diagnosis and treatment of patients with cancerous tumors, pre-malignant conditions, and other diseases or disorders. Typically, in the case of cancer, particularly cancer of the breast, there is a great emphasis on early detection and diagnosis through the use of screening modalities, including physical examination, and particularly mammography, which is capable of detecting very small abnormalities, which are often not palpable during physical examination. When a physician establishes by mammography or other screening modality, e.g., ultrasound, that suspicious circumstances exist, a biopsy must be performed to capture tissue for a definitive diagnosis as to whether the suspicious tissue cells in the lesion are cancerous. Biopsy may be done by an open or percutaneous technique. Open biopsy, which is an invasive surgical procedure involving cutting into the suspicious tissue and directly visualizing the target area, removes the entire mass (excisional biopsy) or a part of the mass (incisional biopsy). Percutaneous biopsy, on the other hand, is usually done with a needle-like instrument through a relatively small incision, performed either blindly or with the aid of an imaging device such as ultrasound, MRI, or the like, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, including the location of the lesion(s) within the body, and no single procedure is ideal for all cases. However, core biopsy is extremely useful in a number of conditions and is being used more frequently by the medical profession.

To arrive at a definitive tissue diagnosis, intact tissue is needed from an organ or lesion within the body. In most instances, only part of the organ or lesion need be sampled. However, the portions of tissue obtained must be representative of the organ or lesion as a whole. In the past, to obtain tissue from organs or lesions within the body, surgery had to be performed to locate, identify and remove the tissue. With the advent of medical imaging equipment (x-rays and fluoroscopy, computed tomography, ultrasound, nuclear medicine, and magnetic resonance imaging) it became possible to identify small abnormalities even deep within the body. However, definitive tissue characterization still requires obtaining adequate tissue samples to characterize the histology of the organ or lesion.

For example, mammography can identify non-palpable (not perceptible by touch) breast abnormalities earlier than they can be diagnosed by physical examination. Most non-palpable breast abnormalities are benign; some of them are malignant. When breast cancer is diagnosed before it becomes palpable, breast cancer mortality can be reduced. However, it is often difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope. Prior to the late 1980's, reaching a definitive tissue diagnosis for non-palpable breast disease required a mammographically guided localization, either with a wire device, visible dye, or carbon particles, followed by an open, surgical biopsy utilizing one of these guidance methods to lead the surgeon to the non-palpable lesion within the breast.

A very successful type of image guided percutaneous core breast biopsy instrument currently available is vacuum-assisted automatic core biopsy device. One such successful biopsy device is shown and disclosed in U.S. Pat. No. 5,526,822 to Burbank et al, which is expressly incorporated by reference herein. This device, known commercially as the MAMMOTOME™ Biopsy System, which is available from Ethicon Endo-Surgery, Inc., a division of Johnson & Johnson, has the capability to actively capture tissue prior to cutting the tissue. Active capture allows for sampling through non-homogeneous tissues. The device is comprised of a disposable probe, a motorized drive unit, and an integrated vacuum source. The probe is made of stainless steel and molded plastic and is designed for collection of multiple tissue samples with a single insertion of the probe into the breast. The tip of the probe is configured with a laterally-disposed sampling notch for capturing tissue samples. Orientation of the sample notch is directed by the physician, who uses a thumbwheel to direct tissue sampling in any direction about the circumference of the probe. A hollow cylindrical cutter severs and transports the tissue samples to a tissue collection chamber for later testing.

While this type of system functions very well as a core biopsy device, there are occasions when it may be useful to have the capability of acquiring a relatively large intact tissue sample. One such core biopsy device is disclosed in U.S. Pat. No. 5,111,928, to Kornberg et al, also expressly incorporated in its entirety by reference herein. In the device disclosed by Kornberg et al., a tissue receiving port is disposed at the distal end of the device and is oriented longitudinally. A disadvantage of this type of device, however, is the inability to acquire a tissue sample having a cross-section larger than that of the cannula through which the sample will be removed. Additionally, it is difficult, using such a device, which obtains cylindrical shaped specimens, to determine whether an entire lesion of interest is being removed or whether a further procedure will be necessary. This is particularly true because most lesions of interest are typically spherical in shape, having a diameter of approximately 1 cm. The only way one can tell whether the entire lesion has been removed using the Kornberg technique is to remove and examine the specimen, determine whether each of the margins of the specimen is "clean," meaning that there is no evidence of lesion, or "dirty," meaning that legion tissue is evident right to the edge of the specimen. Of course, if one or more specimen margins is "dirty," it is almost a certainty that a portion of the lesion remains in the patient, and if the biopsy test results on the lesion are positive, a further surgical procedure will be indicated.

U.S. patent application Ser. No. 09/057,303, priority to which is claimed herein, discloses apparatuses and methods for precisely isolating a target lesion, resulting in a high likelihood of "clean" margins about the lesion. This advantageously will often result in the ability to both diagnose and treat a malignant lesion with only a single percutaneous procedure, with no followup percutaneous or surgical procedure required, while minimizing the risk of migration of possibly cancerous cells from the lesion to surrounding tissue or the bloodstream. Various tissue acquisition instrument embodiments are disclosed for segmenting the target tissue, including embodiments wherein the instrument comprises a cutting element which is extendable radially outwardly and movable circumferentially to define a peripheral margin about a tissue sample, and other embodiments wherein the cutting element is extendable radially outwardly and movable axially to define peripheral margins about the tissue sample.

SUMMARY OF THE INVENTION

According to a first exemplary embodiment of the present invention, a tissue acquisition device useful in retrieving tissue samples from a patient comprises an inner cannula having a proximal end, a distal end, and a longitudinal axis extending between said proximal and distal ends, said inner cannula including a tubular sidewall, a main lumen extending along said longitudinal axis from said proximal end toward said distal end, a small lumen extending longitudinally through said sidewall from said proximal end toward said distal end, and a cutout in said sidewall distal of said small lumen; an outer cannula having a proximal end, a distal end, and a longitudinal axis extending between said proximal and distal ends, said outer cannula including a tubular sidewall, a main lumen extending along said longitudinal axis from said proximal end toward said distal end, and a cutout in said sidewall; a cutting wire positioned in said small lumen, said cutting wire having a proximal end and a distal end and being rotatable and longitudinally extendable in said small lumen, said cutting wire including a cutting loop at a said distal end which extends out of said small lumen; wherein said inner cannula is positioned in said outer cannula main lumen with said inner cannula cutout positioned at the same longitudinal position as said outer cannula cutout.

According to a second exemplary embodiment of the present invention, a system for sampling tissue from a patient comprises a radio frequency (RF) energy generator capable of generating RF energy, and a tissue acquisition device as described above, said cutting wire of said tissue acquisition device in electrical communication with said RF energy generator.

According to a third exemplary embodiment of the present invention, a method of sampling tissue from a patient comprises the steps: inserting a cannula into tissue of a patient, said cannula including a pair of concentric cannulae each having a cutout therein, said cannula including a RF energy cutting loop in said cannula; cutting said tissue along a plane by moving said RF energy cutting loop from a position inside said cannula to a position outside said cannula while applying RF energy to said RF energy cutting loop; cutting said tissue by moving said RF energy cutting loop along a first path extending partially along the length of said cannula while applying RF energy to said RE energy cutting loop; and cutting said tissue along a plane perpendicular to said path by moving said RF energy cutting loop.

According to a fourth exemplary embodiment of the present invention, a tissue acquisition device useful in retrieving tissue samples from a patient comprises a generally cylindrical cannula having a longitudinal axis and a cutout, an electrically energized cutting wire loop arranged generally in a plane substantially parallel to said cannula longitudinal axis, said loop being rotatable about a loop axis which extends generally parallel to said cannula longitudinal axis, said loop axis being offset from said cannula longitudinal axis, whereby, upon rotation of said loop about said loop axis, said loop moves from a location within said cannula to a location extending through said cutout.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 20 is an illustration of yet another embodiment of a cutting loop;

FIG. 21 is a cross-sectional view taken along line 21-21 in FIG. 20; and

FIG. 22 is an illustration of yet another embodiment of an outer cannula.

DESCRIPTION OF THE PREFERRED EMBODIMENTS

Figure 1:
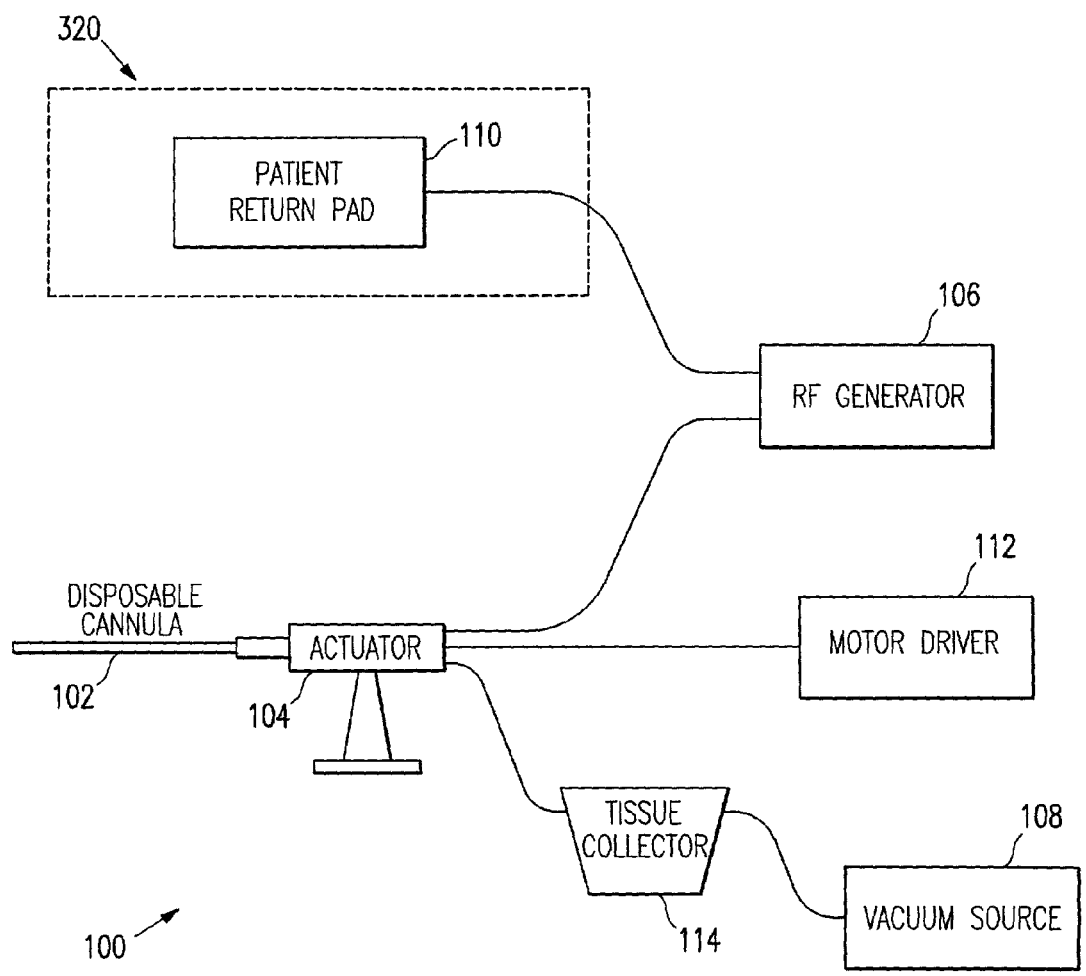
FIG. 1 is an illustration of a first exemplary embodiment of a tissue acquisition system.

Referring to the drawing figures, like reference numerals designate identical or corresponding elements throughout the several figures.

In FIG. 1, a system 100 for sampling or removing tissue from a patient (not illustrated), includes a cannula 102, which is preferably constructed of materials so that it can economically be disposable. System 100 further includes an actuator 104 to which cannula 102 is removably attached. Actuator 104 is preferably non-disposable, i.e., is constructed of materials and includes components which are intended to be reused. Actuator 104 is the interface between cannula 102 and an RF generator 106 and vacuum source 108, and also includes at least two motors (not illustrated): a first motor which rotates an outer cannula (not illustrated in FIG. 1; see FIG. 4) of the cannula 102, as well as rotates a cutting wire (not illustrated in FIG. 1; see FIGS. 2 and 5a-5d); and a second motor which moves the cutting wire longitudinally. Additionally, actuator 104 includes switches and proximity sensors which provide control signals for controlling the first and second motors, RF generator 106, and vacuum source 108:

Actuator 104 is connected to and in electrical communication with RF generator 106, which is connected to and in electrical communication with a patient return pad 110 for the RF cutting system, described in greater detail below. The switches in actuator 104 (not illustrated) control the application of RF energy by the cannula 102, as described in greater detail below. A motor driver 112 is also connected to actuator 104, and provides power to the motors in actuator 104. Motor driver 112 receives signals from the switches and proximity sensors in actuator 104, which are used as feedback control signals to control the states of the motors. Vacuum source 108 preferably includes a vacuum pump or other suitable source of vacuum (not illustrated), and is preferably controllable to at least two vacuum pressure levels. The vacuum pump can also be controllable over a continuum of pressure levels. A tissue collector 114, such as a vacuum jar or similar device, is positioned between vacuum source 108 and cannula 102, and collects tissue sampled or removed from a patient which have been drawn from cannula 102 by the vacuum generated by vacuum source 108. Tissue collector 114 can be reusable or, preferably, disposable.

Figure 2:
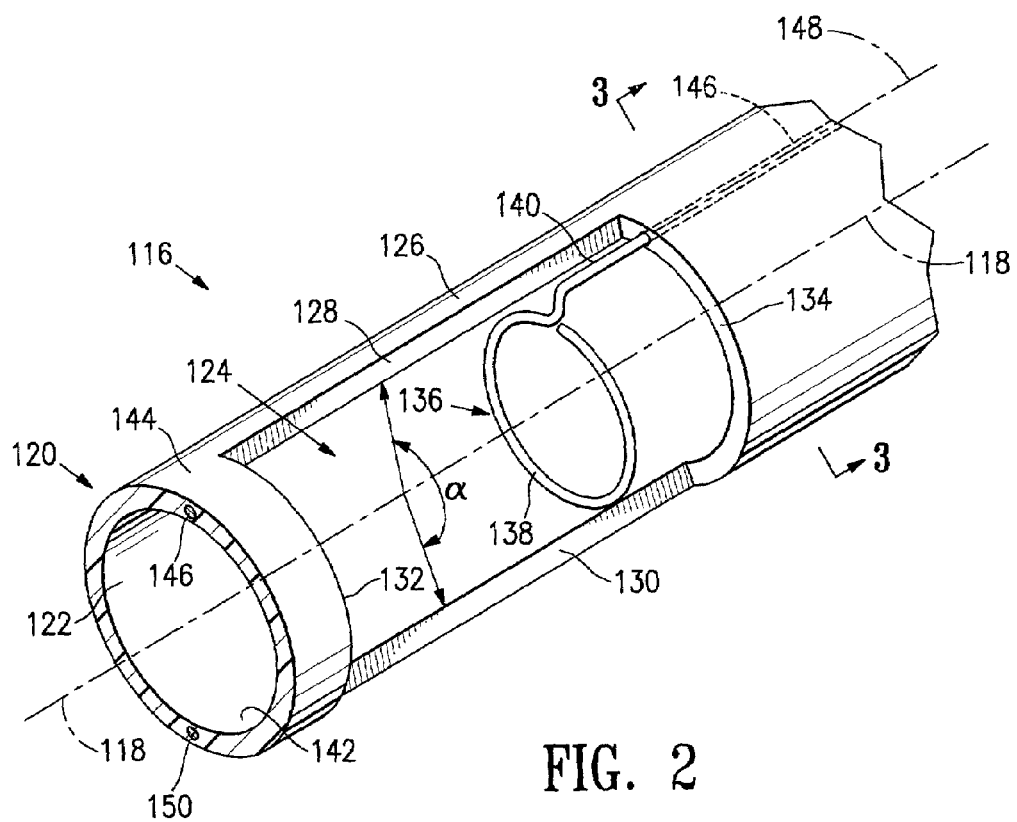
FIG. 2 is a schematic illustration of a portion of an inner cannula of the tissue acquisition system illustrated in FIG. 1.

FIG. 2 illustrates a distal portion of an inner cannula 116 which forms a part of cannula 102. Inner cannula 116 is generally tubular, and has a longitudinal axis 118 which extends between a distal end 120 and a proximal end (not illustrated). Inner cannula 116 includes a main tissue lumen 122 which extends longitudinally from the proximal end to the distal end 120. Inner cannula 116 is preferably formed of a relatively rigid, electrically non-conductive, and biocompatible material. The proximal portions of inner cannula 116, not illustrated in FIG. 2, are generally tubular like the distal portions thereof illustrated in FIG. 2.

Inner cannula 116 further includes a cutout, slot, window, or fenestration 124 through the sidewall 126 of inner cannula 116, which exposes main lumen 122 to the exterior of the inner cannula. Cutout 124 is preferably formed by two sidewalls 128, 130, a distal endwall 132, and a proximal endwall 134. More preferably, sidewalls 128, 130 are longitudinally extending, i.e., extend parallel to axis 118, and endwalls 132, 134 extend perpendicular to sidewalls 128, 132. The angular separation of sidewalls 128, 130, that is, the angle α which is defined between sidewalls 128, 130, is selected so that the cutout 124 is large enough to allow a cutting loop 138 of a cutting wire 136 to be rotated in and out of main lumen 122, as described in greater detail below. Angle α is typically about 180°, although other values for angle α are within the spirit and scope of the invention as will be readily apparent to one of ordinary skill in the art.

Inner cannula 116 is optionally provided with a lubricious coating 142 on the inner side of sidewall 126, which allows a tissue sample to be more easily drawn along main lumen 122. Inner cannula 116 is also optionally provided with a lubricious coating 144 on the outer side of sidewall 126, which allows the inner cannula to be more easily rotated within an outer cannula (see FIG. 4) of cannula 102.

A cutting wire 136 is provided in inner cannula 116. Cutting wire 136 includes a cutting loop 138 and a longitudinally extending actuating portion 140. Actuating portion 140 is slidably received in a passageway which extends from the proximal end of cannula 102 to the region of cutout 124. In the embodiment illustrated in FIG. 2, the passageway which receives actuating portion 140 is a small, second lumen 146 formed in sidewall 126 of inner cannula 116. Alternatively, as illustrated in FIG. 3c, the passageway can take the form of a channel 146' formed in the external surface of inner cannula 116, in which actuating portion 140 is slidably and rotatably received. Channel 146' cooperates with the internal surface of an outer cannula 152 (see FIG. 4a) to retain actuating portion 140 in channel 146'. According to yet another embodiment, the passageway can be formed as a channel 146" in the inner surface of outer cannula 152, as illustrated in FIG. 3d (see also FIG. 4a). According to yet another embodiment, illustrated in FIG. 3e, the passageway is formed as two shallower channels 149, 151, one formed in each of the external surface of inner cannula 116 and the internal surface of outer cannula 152. In the embodiment illustrated in FIG. 3e, one of shallow channels 149, 151 (channel 151 in FIG. 3e) has a much larger circumferential length which describes an angle ϵ, than the other shallow channel, to allow inner cannula 116 and outer cannula 152 to rotate relative to each other without being locked by actuating portion 140, for reasons described in greater detail below. Preferably, angle ϵ is greater than or equal to angles α and β, described below with reference to FIGS. 4a and 4b. Lumen 146 or channels 146', 146", or 149 and 151 are optionally also coated with a lubricious material to facilitate sliding cutting wire 136 therethrough.

In the embodiment illustrated in FIG. 2, cutting loop 138 is a generally circular and closed loop, and preferably lies in a plane perpendicular to a longitudinal axis 148 of actuating portion 140 and lumen 146. Cutting loop 138 can take forms other than a generally circular closed loop, as described in greater detail below. FIG. 2 illustrates lumen 146 continuing on the distal side of cutout 124; optionally, lumen 146 terminates at proximal endwall 134 and opens into cutout 124.

Cutting loop 138 is both longitudinally extendable in cutout 124, and rotatable into and out of lumen 122, because actuating portion 140 is slidably and rotatably received in the passageway. As discussed above with reference to angle α, the size of cutout 124 is selected so that cutting loop 138 is rotatable from a first position (illustrated in FIG. 2) in which the cutting loop is entirely contained within inner cannula 116, and a second position in which the cutting loop has been rotated around axis 148 so that almost all of the cutting loop has passed through the cutout and is outside of the inner cannula. Because actuating portion 140 of cutting wire 136 remains in the passageway, e.g., lumen 146, in both the first and second positions, those portions of cutting loop 138 immediately adjacent the actuating portion 140 will not extend beyond the outer wall of sidewall 126 in the second position.

Lumen 146 is preferably located in sidewall 126 so that it intersects proximal endwall 134 at a location significantly closer to one of sidewalls 128, 130, than the other of the sidewalls of cutout 124. While lumen 146 can, in a less preferred embodiment, be centered between sidewalls 128, 130, locating lumen 146 so that actuating portion 140 of cutting wire 136 is immediately adjacent one of sidewalls 128, 130 allows cutting loop 138 to be made much larger than if lumen 146 were closer to being centered. Thus, locating lumen 146 in sidewall 126 immediately adjacent sidewall 128, as illustrated in FIG. 2, allows for a larger cutting loop 138, because the distance between axis 148 and the opposite sidewall (130, as illustrated in FIG. 2) is larger, thus providing more space for the cutting loop to rotate out of lumen 122. This allows cutting loop 138 to be relatively large. Inner cannula 116 further includes an electrical conductor 150 in sidewall 126, which extends from the proximal end to the distal end 120 of the inner cannula. Electrical conductor 150 is provided to provide electrical communication between RF generator 106 and a cutting element (not illustrated in FIG. 2; see FIGS. 6a and 6b) provided on a distal end of cannula 102.

Figure 3A:
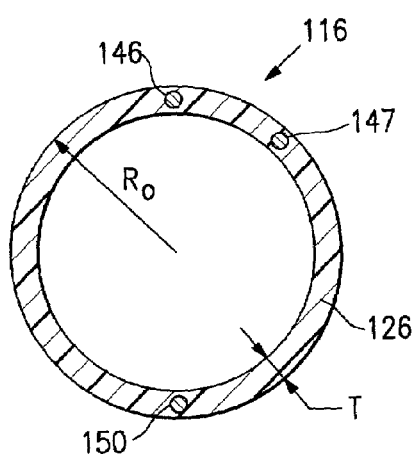
FIG. 3a is a cross-sectional view of the inner cannula illustrated in FIG. 2, taken at line 3-3.
Figure 3B:
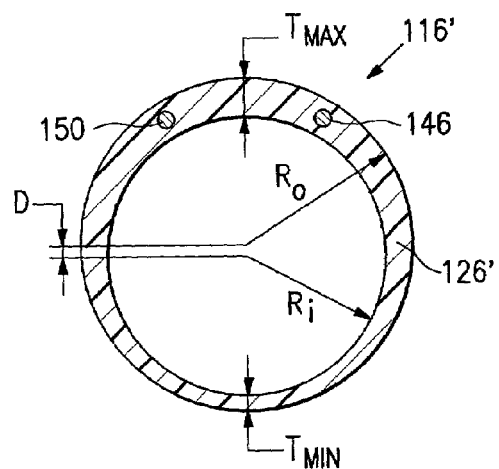
FIG. 3b is a cross-sectional view of an alternate embodiment of the inner cannula illustrated in FIG. 2, taken at line 3-3.
Figure 3C:
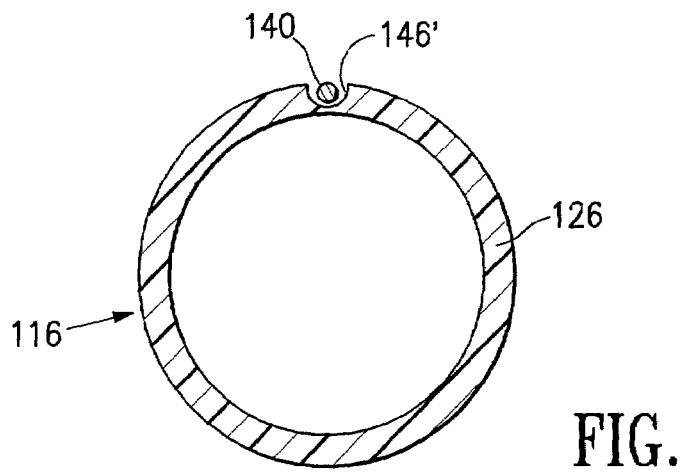
FIG. 3c is a cross-sectional view of another alternate embodiment of the inner cannula illustrated in FIG. 2, taken at line 3-3.
Figure 3D:
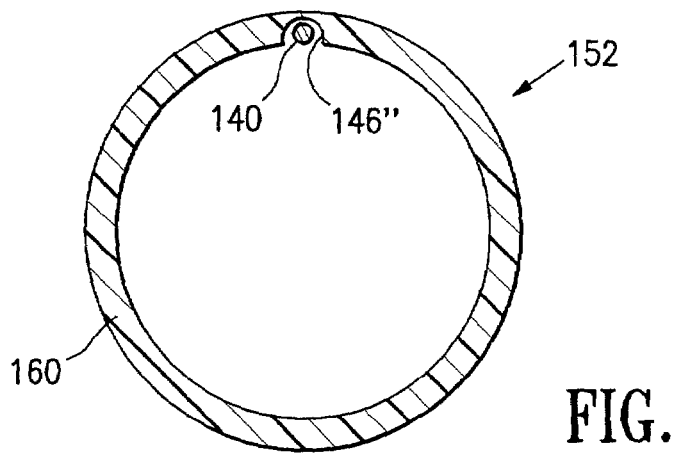
FIG. 3d is a cross-sectional view of yet another alternate embodiment of the inner cannula illustrated in FIG. 2, taken at line 3-3.
Figure 3E:
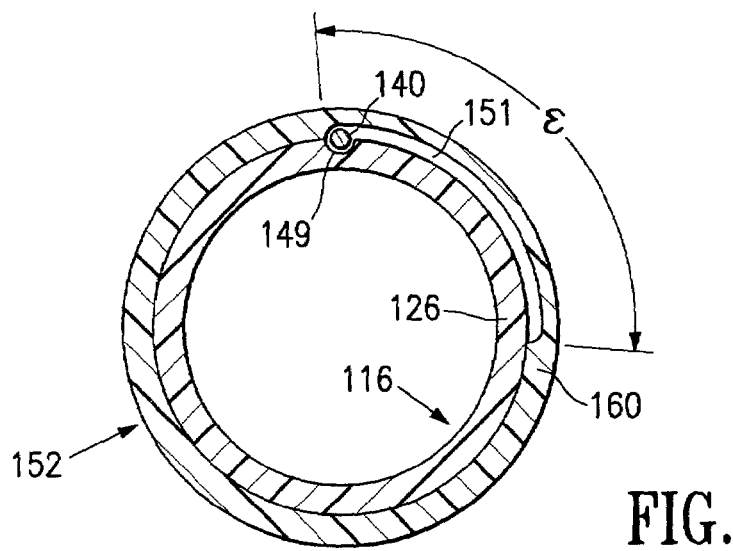
FIG. 3e is a cross-sectional view of another alternate embodiment of the inner cannula illustrated in FIG. 2, taken at line 3-3.

FIGS. 3a and 3b illustrate cross-sectional views of inner cannula 116, as taken at line 3-3. In the embodiment illustrated in FIG. 3a, inner cannula 116 includes a sidewall 126 which has a thickness T, and has an outer radius $R_o$. Actuating portion 140 of cutting wire 136 is not illustrated in FIG. 3a for purposes of clarity, but is located in lumen 146. Inner cannula 116 can optionally further be provided with an additional lumen 147 in sidewall 126, which extends from cutout 124 proximally to the proximal end of the inner cannula, for allowing a practitioner to inject an anesthetic, e.g., Lidocaine, into the tissue to be sampled. Alternatively, such an anesthetic can be injected distally through main lumen 122, in which embodiment lumen 147 can be eliminated. In yet another embodiment (not illustrated), inner cannula 116 is formed slightly undersized relative to outer cannula 152 (see FIG. 4) to form an annular lumen therebetween, for injecting such an anesthetic. In yet another embodiment (not illustrated), a channel can be formed in the exterior surface of inner cannula 116, which together with the inner surface of outer cannula 152 (see FIG. 4) forms a pathway for a practitioner to inject an anesthetic distally to anesthetize the tissue to be sampled.

FIG. 3b illustrates an alternate embodiment, in which an inner cannula 116' has a sidewall 126' with thickness that varies continuously between a maximum $T_{max}$ and a minimum $T_{min}$. Inner cannula 116' includes an outer radius $R_o$ and an inner radius $R_i$, which are taken from two separate longitudinal axes which are separated by a distance D. Lumen and conductor 150 are preferably located in the thickest part of sidewall 126', so that the average thickness of the sidewall can be reduced while still providing lumen 146 and conductor 150.

Figure 4A:
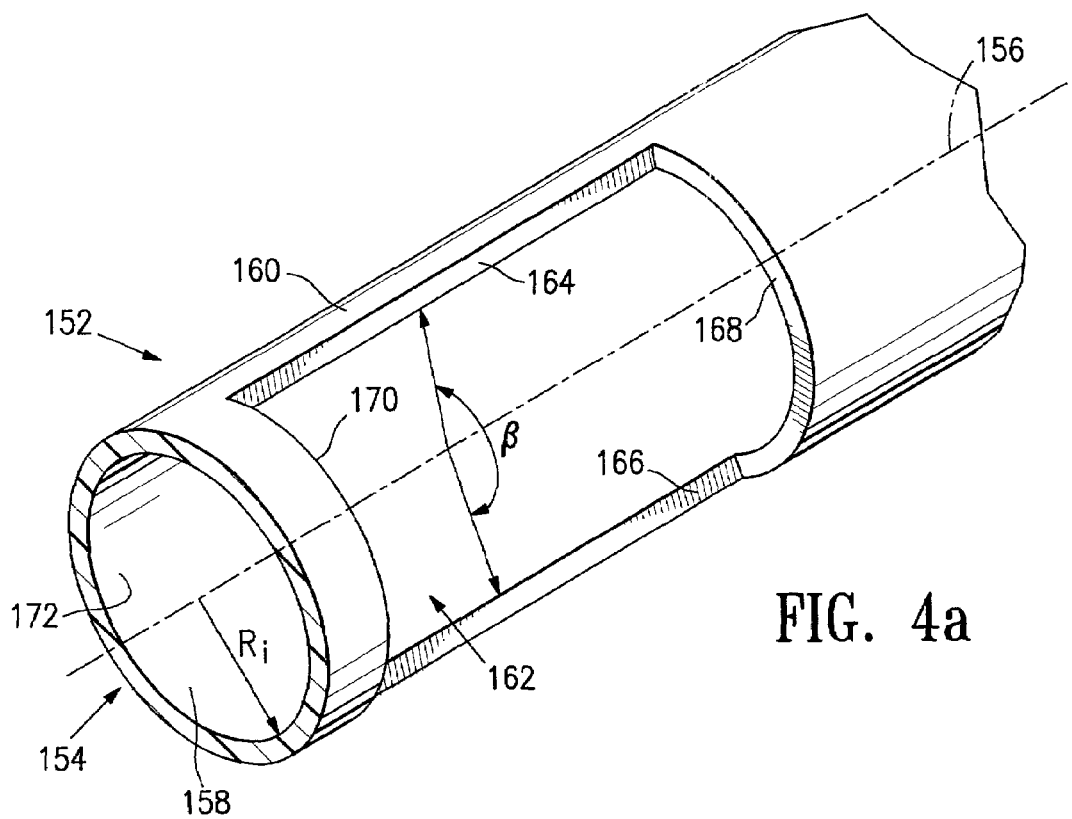
FIG. 4a is a schematic illustration of a portion of an outer cannula of the tissue acquisition system illustrated in FIG. 1.

Turning now to FIG. 4a, a distal portion of an outer cannula 152 of cannula 102 is illustrated in perspective. Outer cannula 152 is generally tubular in construction, and includes a distal end 154, a proximal end (not illustrated), and a longitudinal axis 156 extending between the proximal end and distal end 154. Outer cannula 152 includes a main lumen 158 extending through the outer cannula which has an inner radius $R_i$ selected to be slightly larger than outer radius $R_o$ of inner cannula 116, 116', so that the inner cannula can be slidingly received in the outer cannula main lumen.

Outer cannula 152 includes a sidewall 160 which preferably has a constant thickness formed of a material which is similar to that of inner cannula 116. In a manner similar to inner cannula 116, outer cannula 152 includes a cutout, slot, window, or fenestration 162 formed in sidewall 160. Cutout 162 is formed by sidewalls 164, 166, a proximal endwall 168, and a distal endwall 170. The longitudinal length of cutout 162, i.e., the length of sidewalls 164, 166, is preferably selected to be substantially the same as the length of sidewalls 128, 130 of inner cannula 116. In a less preferred embodiment, the length of sidewalls 164, 166 can be more or less than the length of sidewalls 128, 130.

Preferably, sidewalls 164, 166 are longitudinally extending, i.e., extend parallel to axis 156, and endwalls 168, 170 extend perpendicular to sidewalls 164, 166. The angular separation of sidewalls 164, 166, that is, the angle β which is defined between sidewalls 164, 166, is selected so that the cutout 162 is large enough to allow cutting loop 138 to be rotated through the outer cannula cutout, when inner cannula 116 is in lumen 158. Angle β is typically about 180°, although other values for angle β are within the spirit and scope of the invention as will be readily apparent to one of ordinary skill in the art. The inner surface 172 of lumen 158 is preferably coated with a lubricious material to facilitate rotation of inner cannula 116 relative to outer cannula 152, as described in greater detail below.

Figure 4B:
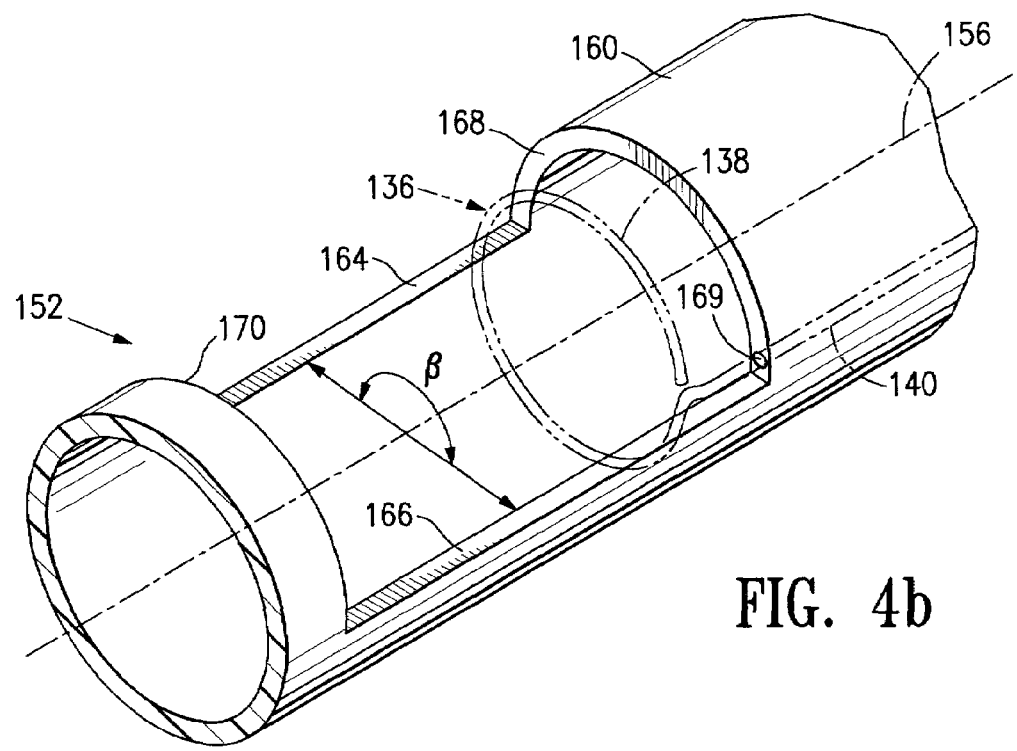
FIG. 4b is a schematic illustration of a portion of an alternate embodiment of an outer cannula of the tissue acquisition system illustrated in FIG. 1.

FIG. 4b illustrates another embodiment of outer cannula 152, in which sidewall 160 is provided with the passageway for cutting wire 136, as a small lumen 169. Cutting wire 136 (illustrated in phantom in FIG. 4b) is located in lumen 169 in a manner similar to lumen 146 (see FIG. 2), such that cutting wire 136 is rotatable and longitudinally extendable therein. In the embodiment illustrated in FIG. 4b, angle β is greater than angle α of inner cannula 116, so that cutting loop 138 will not catch on sidewall 128 as cutting loop 138 is rotating into and out of main lumen 122.

FIGS. 5a-5d illustrate end views of several embodiments of cutting loops usable in the present invention. The cutting loops illustrated in FIGS. 5a-5d are preferably closed cutting loops. The term "closed" within the context of cutting loops as described in the present application refers to geometries of a cutting loop which, when projected onto a plane that is perpendicular to actuating portion 140, form a continuous and closed shape. Thus, the term "closed" includes geometries of cutting loops with free ends that do not touch the rest of the loop, as well as those that do not have free ends. Closed cutting loops have the advantage of allowing a sample of tissue to be cut with a minimum number of cutting strokes.

Figure 5A:
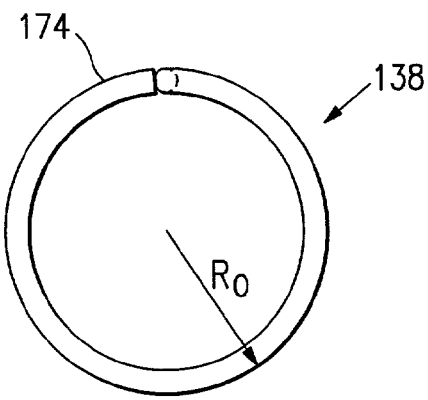
FIG. 5a is a schematic illustration of a portion of a cutting loop of the tissue acquisition system illustrated in FIG. 1.
Figure 5B:
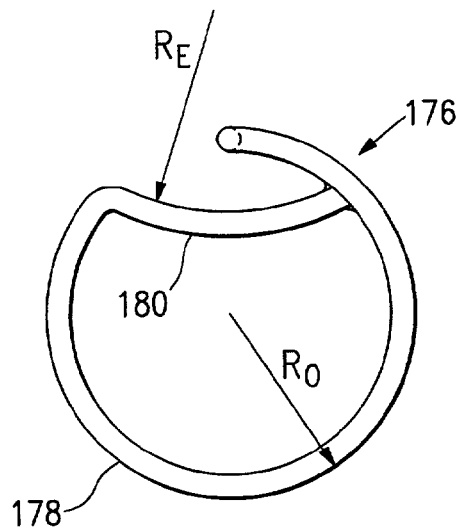
FIG. 5b is a schematic illustration of a portion of an alternate embodiment of a cutting loop of the tissue acquisition system illustrated in FIG. 1.

FIG. 5a illustrates cutting loop 138 as illustrated in FIG. 2. Cutting loop 138 is generally circular, has an outer radius $R_o$, and is closed. Cutting loop 138 includes an end 174 that meets with the rest of the cutting loop and is preferably welded or soldered thereto. FIG. 5b illustrates a cutting loop 176 in accordance with yet another embodiment. Cutting loop 176 includes a generally circular portion 178 describing an outer radius $R_o$, and an end 180 which has been joined to the rest of the cutting loop. End 180 extends inwardly from the circular portion 178, and preferably is curved on a radius RE taken from a point outside of cutting loop 176. End 180 is provided as an inwardly extending curved portion of loop 176 in order to reduce the amount of unsampled space when the cannula 102 is used to sample tissue, as described in greater detail below.

Figure 5C:
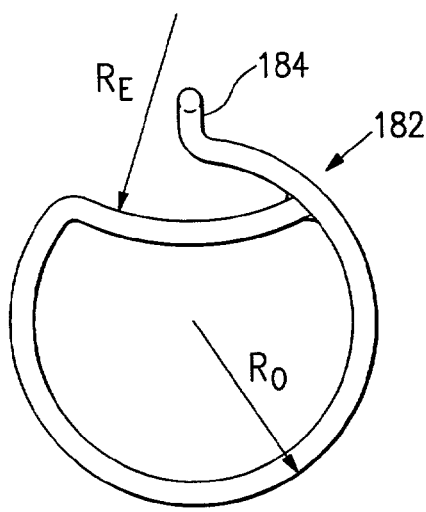
FIG. 5c is a schematic illustration of a portion of another alternate embodiment of a cutting loop of the tissue acquisition system illustrated in FIG. 1.

FIG. 5c illustrates a cutting loop 182 very similar to cutting loop 176, except that the portion 184 of the cutting loop immediately adjacent actuating portion 140 (not illustrated) bends away from the rest of the cutting loop. Portion 184 is bent away in this manner in order to extend cutting loop 182 even farther out of cannula 102 when the cutting wire is rotated out of the inner cannula 116 and the outer cannula 152.

Figure 5D:
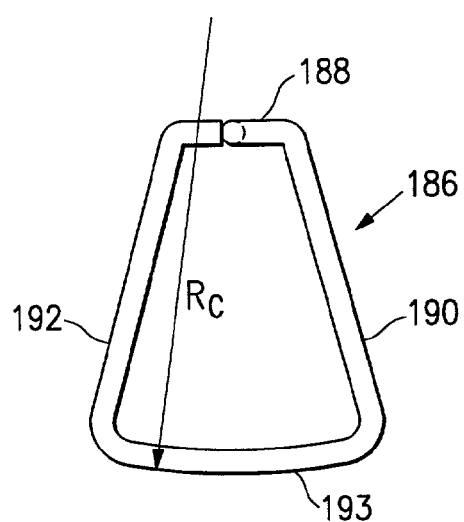
FIG. 5d is a schematic illustration of a portion of yet another alternate embodiment of a cutting loop of the tissue acquisition system illustrated in FIG. 1.

FIG. 5d illustrates a cutting loop 186 in accordance with yet another embodiment. Cutting loop 186 includes an end 188, two radial legs 190, 192 and a middle portion 193 between the radial legs. Middle portion 193, as illustrated in FIG. 5d, curves along a radius $R_C$, although middle portion 193 can alternatively extend linearly between radial legs 190, 192. Radial legs 190, 192 extend generally linearly, so that when cannula 102 is used to gather a plurality of tissue samples around the cannula, the unsampled space around the cannula is minimized.

Cutting loops herein are formed of a material so that the cutting loops can be used as a RF energy cutting loop. Preferably, the cutting loops are formed of stainless steel, tungsten, platinum, or nickel-titanium alloy wire.

Figure 6A:
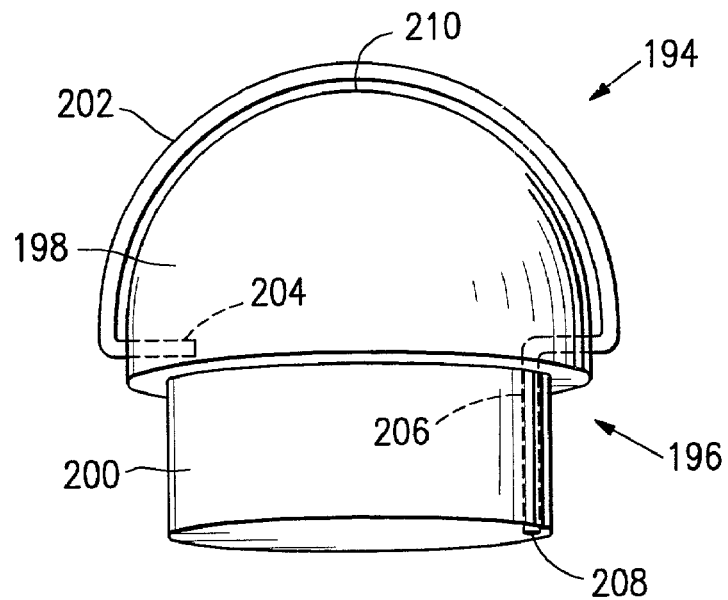
FIG. 6a is a schematic illustration of a distal tip portion of the tissue acquisition system illustrated in FIG. 1.
Figure 6B:
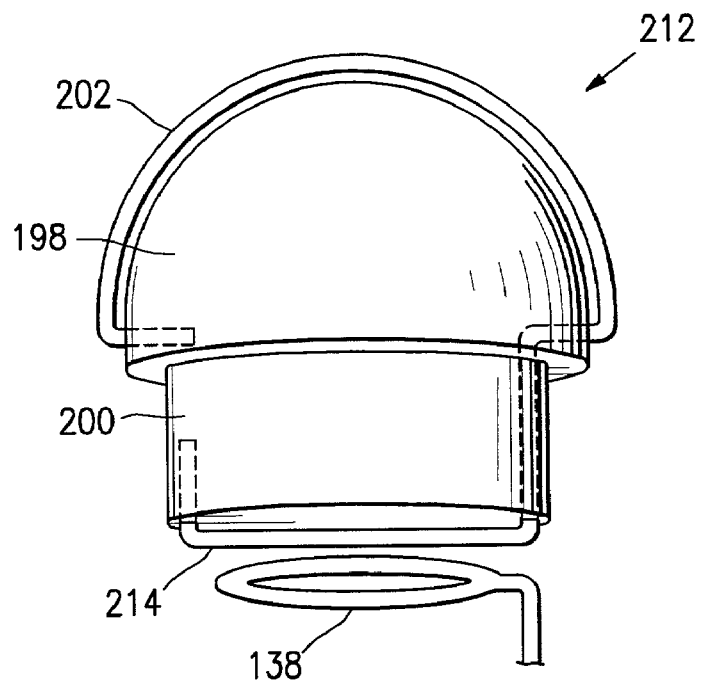
FIG. 6b is a schematic illustration of portions of an alternate embodiment of the tissue acquisition system illustrated in FIG. 1.

FIGS. 6a and 6b illustrate two embodiments of an end plug. In FIG. 6a, an end plug 194 includes a mushroom-shaped body 196 having a dome-shaped head 198 and a cylindrical base 200. End plug 194 is formed of a medical grade polymer, preferably high density polyethylene (HDPE). A cutting wire 202 is attached to head 198 on radially opposite sides of the head, and is embedded in the head at a free end 204 and a connecting portion 206. Connecting portion 206 extends through base 200, and terminates at a connector 208. Connector 208 is positioned on base 200 so that it lines up with and is in physical and electrical contact with conductor 150 in inner cannula 116 when end plug 194 is assembled with inner cannula 116 and outer cannula 152. Cutting wire 202 is formed of a material which allows the cutting wire to act as a RF cutting element when assembled with inner cannula 116 and when RF generator 106 is connected to the proximal end of conductor 150.

Cutting wire 202 is provided distal of the distal end 210 of end plug 194 so that cannula 102 can be easily inserted into tissue, the RF energy from RF generator 106 passing through conductor 150 and to cutting wire 202. Cutting wire 202 creates a slit in the tissue into which it is pressed, which allows cannula 102 to advance into tissue and to a site at which a tissue sample is desired, with a minimum of trauma to the patient. The use of cutting wire 202 also is advantageous because the RF cutting which is provided therewith allows entry of cannula 102 into target tissue to be made with much less pushing force than prior devices, and in particular than prior devices which rely on a sharpened or pointed cannula for entry into a target tissue. Similarly advantageous is that the use of RF energy cutting wires, including cutting wire 202 and cutting loops 138, 176, 182, and 186, may lead to significant reductions in bleeding.

FIG. 6b illustrates an end plug 212 in accordance with yet another exemplary embodiment. End plug 212 is substantially similar to end plug 194, and therefore only the differences between end plug 194 and end plug 212 will be described. Instead of connector 208, end plug 212 includes a connector loop 214 which extends out of and then returns back into base 200. Connector loop 214 is shaped and sized to make physical and electrical contact with a cutting loop as described above, so that the cutting loop can act as a RF energy conductor for cutting wire 202 in the place of a conductor 150 extending through inner cannula 116. In FIG. 6b, cutting loop 138 is illustrated, although any of the cutting loops described herein can alternatively be used; connector loop 214 is shaped and sized to make electrical contact with the cutting loop with which it is intended to be used. To utilize the advantages of end plug 212, cutout 124 in inner cannula 116 should extend to the distal end of the inner cannula, so that the cutting loop can extend to the end plug.

According to yet another embodiment (not illustrated), connector loop 214 can be replaced by an electrically conductive plate positioned on the proximal end surface of end plug 212, and electrically connected to connecting portion 206. A plate is advantageously used so that a single design of end plug can be used with any cutting loop, because such a plate makes physical and electrical contact with cutting loops having any point which will contact the plate.

Figure 7:
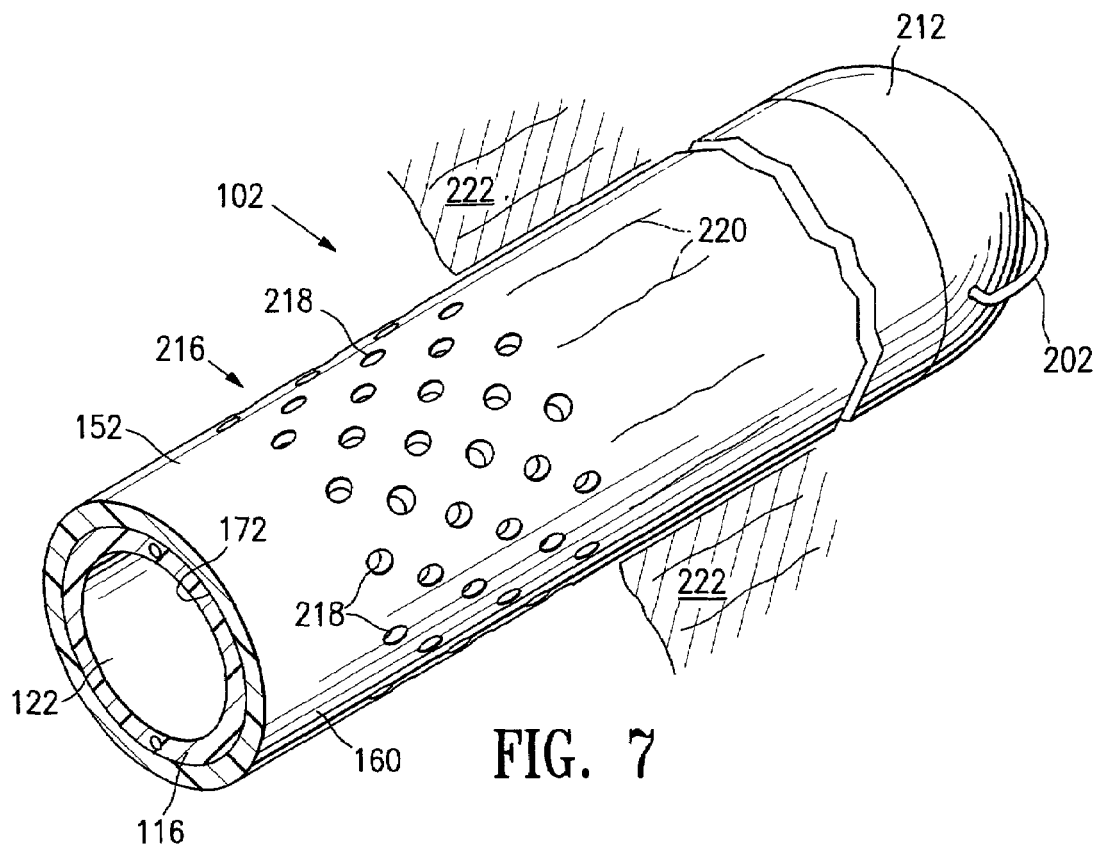
FIG. 7 is a schematic illustration of proximal portions of a cannula.

FIG. 7 illustrates a schematic perspective view of portions of inner cannula 116, outer cannula 152, and an end plug 194 or 212, assembled together as cannula 102. Outer cannula 152 preferably includes a mesh, screen, or array 216 including a plurality of openings 218 through sidewall 160 of the outer cannula. Screen 216 is provided along outer cannula 152 proximal of cutout 162, for aspirating any vapors 220, including smoke and odors, which may be evolved during the use of the RF cutting elements of cannula 102. Vapors 220 which travel proximally along cannula 102 and which exit an opening in the tissue 222 being sampled can be aspirated through openings 218 and into main lumen 122 of inner cannula 116. Inner cannula 116 is also provided with a mesh, screen, or array through its sidewall 126, as described in greater detail below with reference to FIG. 8.

Figure 8:
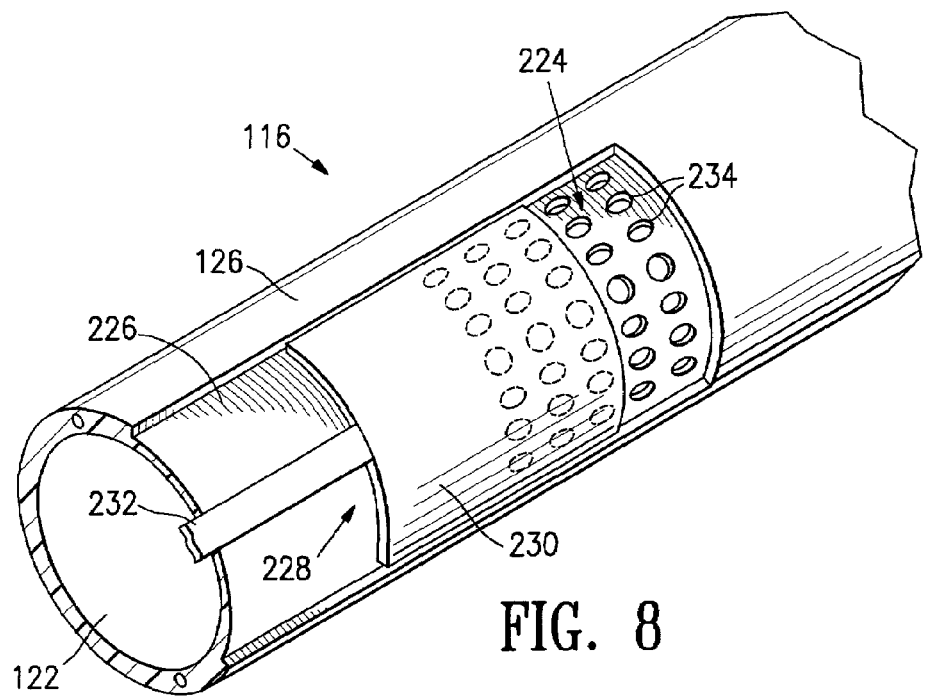
FIG. 8 is a schematic illustration of proximal portions of an inner cannula.

FIG. 8 illustrates a perspective view of proximal portions of inner cannula 116, proximal of the portions illustrated in FIG. 2. Inner cannula 116 includes a mesh, screen, or array 224 through sidewall 126. Sidewall 126 is preferably provided with a longitudinally extending recess 226 which extends partially through sidewall 126, and in which screen 224 is formed. Similar to screen 216 described above, screen 224 communicates main lumen 122 of inner cannula 116 with the exterior of the inner cannula. When inner cannula 116 is positioned in main lumen 172 of outer cannula 152, screen 224 lies under screen 216, so that vacuum that is applied to main lumen 122 of the inner cannula is effective to aspirate vapors through both screens and into the inner cannula main lumen proximal of any tissue samples which may have been collected.

Inner cannula is also optionally provided with aspiration regulator 228, which is positioned in recess 226. Recess 226 is provided to allow aspiration regulator 228 to slide between inner cannula 116 and outer cannula 152 to selectively cover or uncover portions of screens 216 and 224. In yet another embodiment, neither recess 226 nor aspiration regulator 228 is provided, in which embodiment vapor aspiration is regulated by regulating only the vacuum applied to main lumen 122. In the embodiment illustrated in FIGS. 7 and 8, aspiration regulator 228 includes a curved plate 230 and an actuation member 232 extending proximally from the curved plate. Curved plate 230 is curved to conform to the outer diameter of inner cannula 116 in recess 226. By moving actuation member 232 proximally and distally, the number of openings 234 which can fluidly communicate with openings 218 is controlled, thereby regulating the strength of aspiration through screen 216 and screen 224 when vacuum is applied to main lumen 122.

A method of operating the above-described apparatus for collecting tissue samples will now be described with reference to FIGS. 9-14, and with reference to Table 1 below. Table 1 describes the status of several of the elements of system 100 during use thereof.

TABLE 1

| STEP | MODE OF OPERATION | RF ENERGY TIP | RF ENERGY LOOP | VACUUM SOURCE | TISSUE CHANNEL |
|------|-------------------|---------------|----------------|---------------|----------------|
| 1 | Initial entry into tissue until located | ON | OFF | OFF | CLOSED |
| 2 | Opening of Tissue Channel | OFF | OFF | OFF | OPENING |
| 3 | Deployment of Cutting Wire | OFF | ON | OFF | OPEN |
| 4 | Closing of Tissue Channel | OFF | OFF | OFF | CLOSING |
| 5 | Distal Cutting of Tissue | OFF | ON | ON | CLOSED |
| 6 | Opening of Tissue Channel | OFF | OFF | ON | OPENING |
| 7 | Detachment of Tissue | OFF | ON | ON | OPEN |
| 8 | Closing of Tissue Channel | OFF | OFF | ON | CLOSING |
| 9 | Retrieval of Tissue Sample and Resetting of Cutting Wire Position | OFF | OFF | ON | CLOSED |

In Table 1, the column labeled "Tip" refers to whether RF generator 106 is activated to apply RF energy to cutting wire 202, "Loop" refers to whether RF generator 106 is activated to apply RF energy to cutting loop 138, 176, 182, and/or 186, and the status of the "Tissue Channel" refers to the radial alignment of cutouts 124, 162: when the cutouts are radially aligned, an open "tissue channel" is formed into cannula 102 through both cutouts, and when the cutouts are not radially aligned, the tissue channel is closed.

Figure 9:
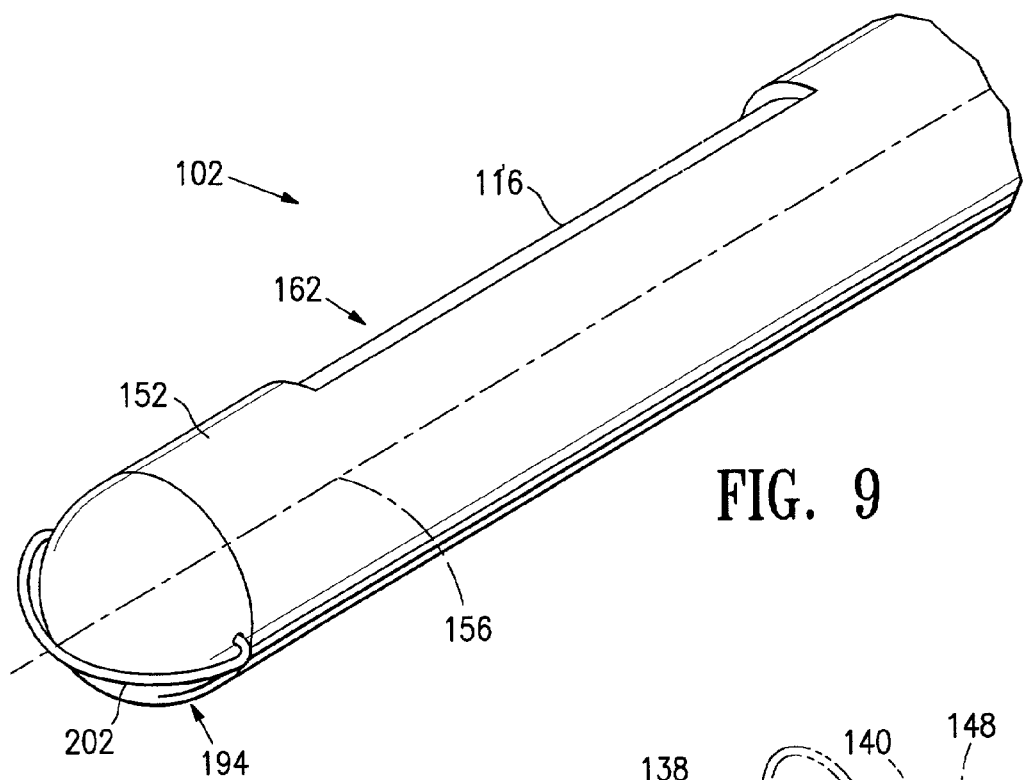
FIGS. 9-14 are perspective illustrations of a cannula, illustrating an exemplary process of sampling tissue.
Figure 10:
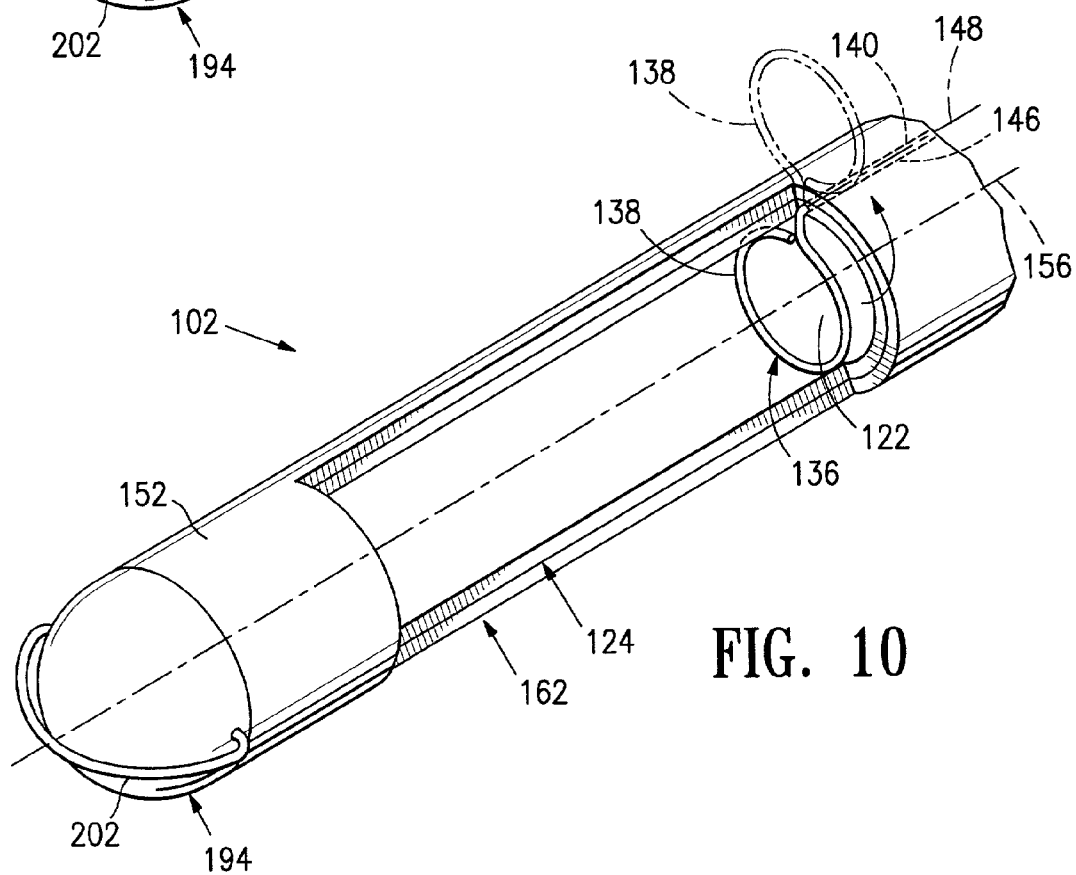

FIG. 9 illustrates the distal end of cannula 102 in a condition to be inserted into tissue to be sampled. The tissue channel in the fully closed position; inner cannula 116 is visible through cutout 162, but cutout 124 is not radially aligned with cutout 162. End plug 194 (or 212, if desired) has been mounted on the distal end of the inner cannula or the outer cannula. As stated in Table 1 above, step 1 proceeds with the advancement of cannula 102 into the tissue with RF energy being applied to cutting wire 202, which allows cannula 102 to be easily advanced into the tissue to the target site. Once the target site has been accessed, as assessed by measuring the advancement of the cannula into the tissue and comparing with prior measurements, or by ultrasound, MRI, X-ray, or other imaging devices, outer cannula 152 is caused to rotate relative to inner cannula 116. This relative rotation, step 2 above, is continued until the tissue channel is completely open, i.e., the maximum overlap between cutouts 124 and 162 (corresponding to the smaller of angles α and β). This orientation is illustrated in FIG. 10, wherein cutting loop 138 is also illustrated. Cutting loop 138 is in a retracted position, during insertion of cannula 102 into the tissue and the relative rotation of the inner and outer cannulae, which shields the patient from premature exposure to the cutting wire 136.

Step 3 above is then commenced, wherein cutting wire 136, including cutting loop 138, is rotated around longitudinal axis 148, which causes the cutting loop to pass through both cutouts 124, 162 and into the tissue into which cannula 102 has been inserted. During rotation of cutting loop 138, RF energy is allowed to flow to cutting loop 138, so that the cutting loop cuts tissue as it rotates. Cutting loop 138 is rotated until it is entirely out of cannula 102, thus forming a first, planar cut in the tissue to be sampled. Application of RF energy through cutting loop 138 is then ceased.

Figure 11:
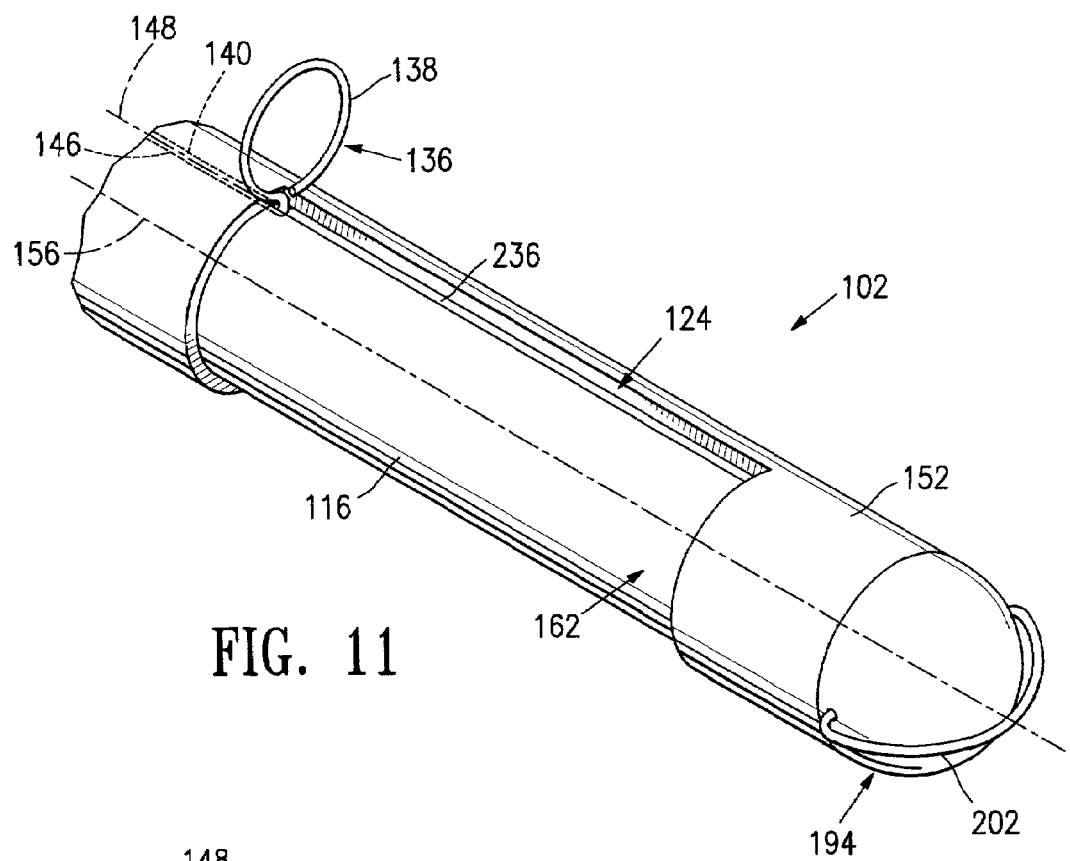
Figure 12:
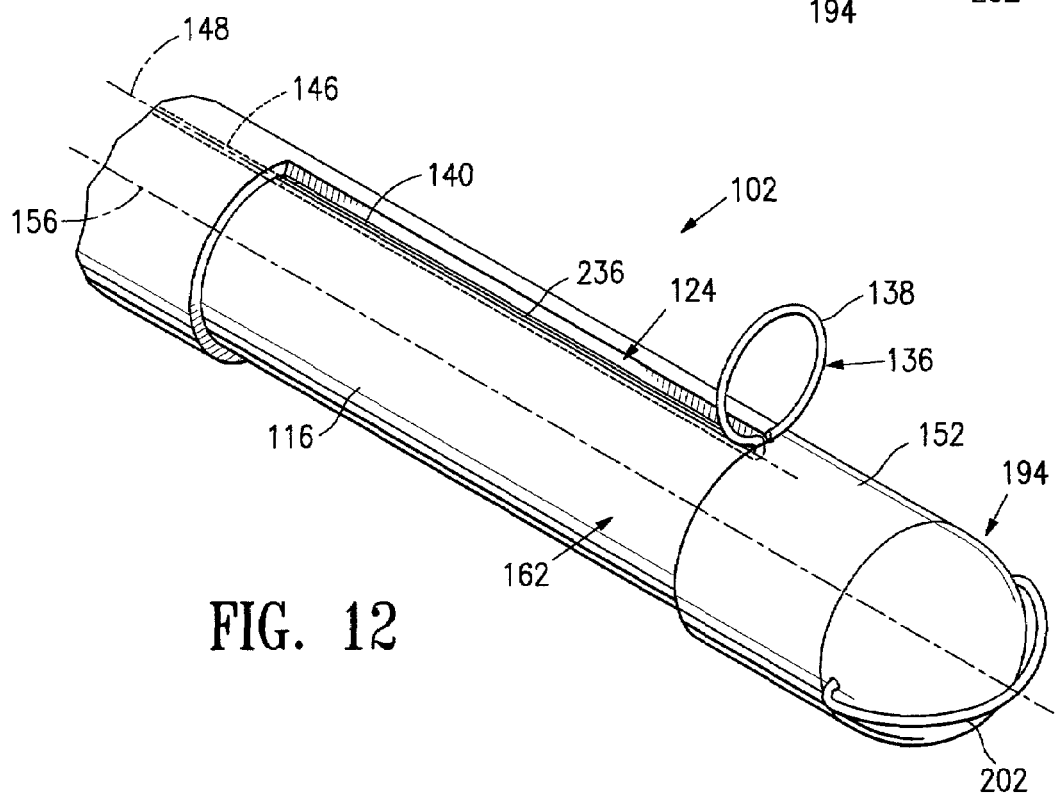

In step 4, outer cannula 152 is rotated to close the tissue channel, except for a small slot 236 between a sidewall of cutout 124 and a sidewall of cutout 162 which is present because cutting wire 136 still extends through the cutouts, and prevents the outer cannula from rotating to completely close the tissue channel. This stage is illustrated in FIG. 11. The vacuum source is then preferably activated to begin drawing tissue close to cannula 102, and in particular toward slot 236. If it is necessary to draw the tissue closer to cannula 102, vacuum source 108 can be adjusted to increase the negative pressure applied through lumen 122. Alternatively, slot 236 can be widened by rotating inner cannula 116, outer cannula 152, or both to widen slot 236.

Step 5 is then initiated, whereby RF energy is again allowed to flow to cutting loop 138, and cutting wire 136 is pushed in lumen 146, which pushes the cutting loop through the tissue distal of the loop and toward the distal end of the tissue channel. At the end of this cutting stroke, illustrated in FIG. 12, cutting loop 138 has formed a second, cylindrical cut in the tissue to be sampled. RF generator 106 is then deactivated, and cutting loop 138 ceases to cut. The distal end of the cylinder of tissue cut in step 5 remains attached to the tissue mass in which cannula 102 has been inserted.

Step 6 is then performed, by which outer cannula 152 is again rotated relative to inner cannula 116 to open the tissue channel to its maximum size. Alternatively, outer cannula 152 and inner cannula 116 can be counter-rotated away from each other, either serially or simultaneously, to open the tissue channel. Rotating both cannulae has the advantage of automatically centering the cylindrical tissue sample over the tissue channel, which aids in drawing it into the main channel 122. During counter-rotation of the cannulae, cutting wire 136 can be slightly rotated, so as not to cut the tissue sample (yet), or can be held in position, which will result in some planar cutting of the tissue sample.

Figure 13:
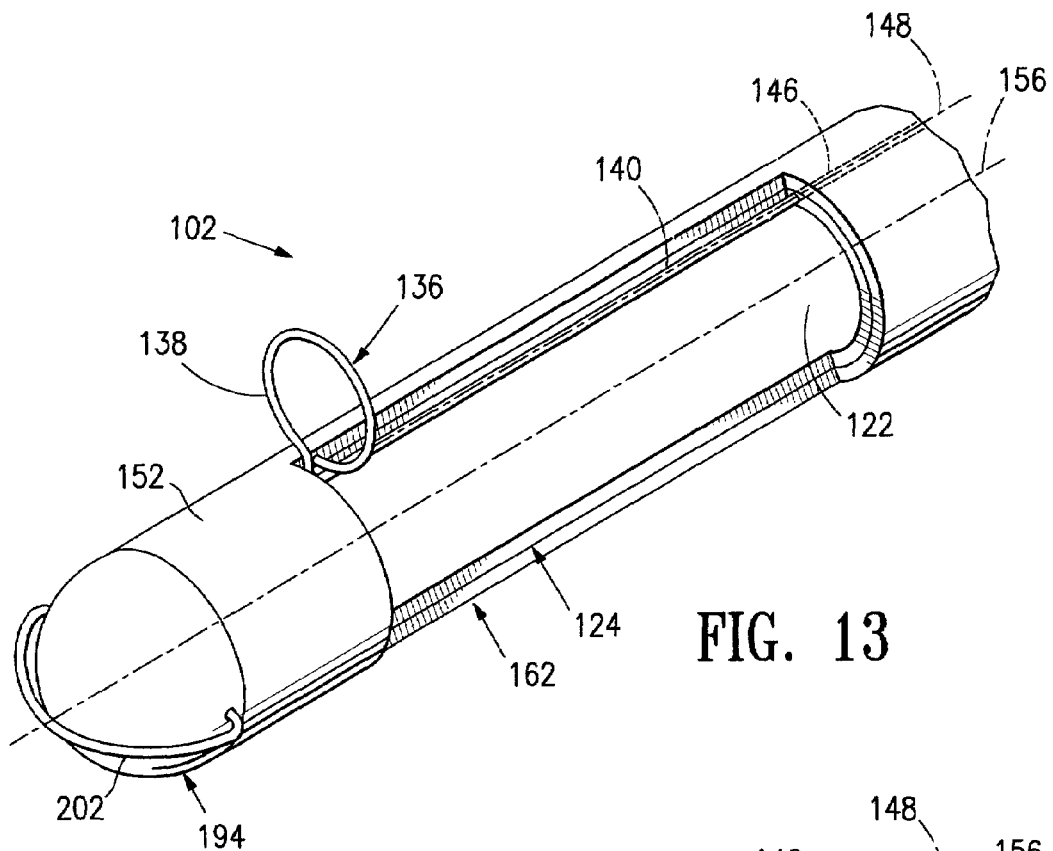

As the tissue channel is widened, vacuum is applied to main lumen 122, which draws the cylindrical tissue sample, beginning with the proximal end thereof, into the main lumen of inner cannula 116. The tissue sample is still connected to the tissue mass, as discussed above. Once outer cannula has been rotated to maximize the size of the tissue channel, step 7 is commenced. RF energy is again allowed to flow to cutting loop 138, and the cutting loop is rotated about axis 148 back into main lumen 122. As cutting loop 138 is rotated, it performs a third, planar cut in the tissue to be sampled, at the distal end of the cylinder of tissue formed by the first two cuts. This step is illustrated in FIG. 13. Vacuum is applied to main lumen 122, which draws the distal end of the tissue sample, just cut by cutting loop 138's rotation back into the main lumen.

Figure 14:
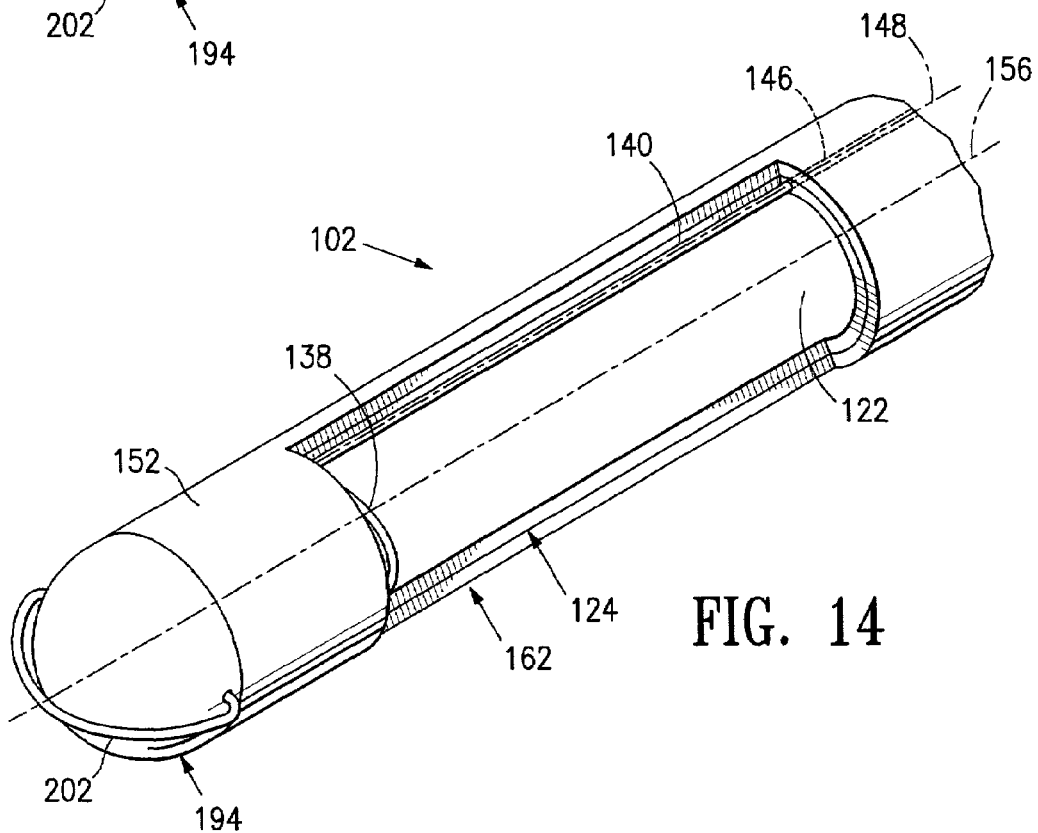

When cutting loop 138 has been rotated completely back into main lumen 122, illustrated in FIG. 14, step 8 can start, in which vacuum continues to be applied to the main lumen, and outer cannula 152 is again rotated to close the tissue channel completely. RF energy is then cut off from cutting loop 138. Because cutting wire 136 is fully within outer cannula 152, the outer cannula can be rotated to completely close the tissue channel, i.e., there is no overlap of cutouts 124, 162. Step 9 is then performed, whereby vacuum is applied to main lumen 122 to draw the cylindrical tissue sample proximally through the main lumen and into tissue collector 114. Cutting wire 136 is then retracted to the proximal end of cutout 124, which completes one cycle. Cannula 102 is then rotated in place about axis 118 so that cutting wire 136 will be adjacent an unsampled volume of tissue, and the cycle is repeated beginning with step 1. These cycles are repeated until cannula 102 has been rotated completely around axis 118, at which time sampling is complete, and cannula 102 can be withdrawn from the patient.

In accordance with yet another embodiment, system 100 can be used to perform a somewhat different process of obtaining a tissue sample. Table 2 below describes the steps of this latter embodiment, which can be described as a "one-stroke" version of the above-described process, which first process can be described as a "two-stroke" process. By "two-stroke" it is meant that cutting loop makes two trips along its path across the tissue channel: one distally to cut, one proximally to reset at the end of the cycle. In this latter, "one-stroke" embodiment of a process, the proximal return stroke of the cutting loop is utilized as a cutting stroke for a different, adjacent cylinder of tissue.

TABLE 2

| STEP | MODE OF OPERATION | RF ENERGY TIP | RF ENERGY LOOP | VACUUM SOURCE | TISSUE CHANNEL |
|---|---|---|---|---|---|
| 1 | Initial entry into tissue until located | ON | OFF | OFF | CLOSED |
| 2 | Opening of Tissue Channel | OFF | OFF | OFF | OPENING |
| 3 | Deployment of Cutting Wire | OFF | ON | OFF | OPEN |
| 4 | Closing of Tissue Channel | OFF | OFF | OFF | CLOSING |
| 5 | Distal Cutting of Tissue | OFF | ON | ON | CLOSED |
| 6 | Opening of Tissue Channel | OFF | OFF | ON | OPENING |
| 7 | Detachment of Tissue | OFF | ON | ON | OPEN |
| 8 | Closing of Tissue Channel | OFF | OFF | OFF | CLOSING |
| 9 | Retrieval of Tissue Sample | OFF | OFF | ON | CLOSED |
| 10 | Rotate Cannula to Next Site | OFF | OFF | OFF | CLOSED |
| 11 | Opening tissue channel | OFF | OFF | OFF | OPENING |
| 12 | Deployment of Cutting Wire | OFF | ON | OFF | OPEN |
| 13 | Closing of Tissue Channel | OFF | ON | OFF | CLOSING |
| 14 | Proximal Cuffing of Tissue | OFF | ON | ON | CLOSED |
| 15 | Opening of Tissue Channel | OFF | OFF | ON | OPENING |
| 16 | Detachment of Tissue | OFF | ON | ON | OPEN |

Steps 1-9 of the process described in Table 2 are identical to steps 1-9 of the "two-stroke" process. At step 10, cannula 102 is rotated around axis 118 so that the (closed) tissue channel is under an unsampled tissue site. The tissue channel is then opened at step 11, followed by redeploying cutting loop 138 from within cannula 102. Different from the "two-stroke" process described above, the cutting loop has not been repositioned at the opposite end of the tissue channel; instead, the cutting loop remains in the position after the third cut of the previous tissue sample, and essentially "back-tracks" through another tissue site on the subsequent stroke.

Accordingly, at step 12 cutting loop 138 is redeployed out of the tissue channel by rotating cutting wire 136. Cutting wire 136 is energized during step 12, causing cutting loop 138 to make a first planar cut in the new tissue site. The tissue channel is then closed in step 13, and, in step 14, a second, cylindrical, proximal cut is made in the second tissue sample with cutting loop 138. The tissue channel is then opened in step 15, and vacuum, preferably high vacuum, is applied to main lumen 122, and the third, planar, proximal cut is made by rotating cutting wire 136 back into the proximal end of the open tissue channel in step 16. These cycles are repeated until cannula 102 has been rotated completely around axis 118, at which time sampling is complete, and cannula 102 can be withdrawn from the patient.

Yet another exemplary embodiment of a process for sampling tissue is similar to the "one-stroke" process described above, and includes fewer steps. The "one-stroke" process is performed up to the point where all three cuts have been made with cutting loop 138. Instead of closing the tissue channel, and thus enclosing cutting loop 138 in main lumen 122, the cutting loop 138 is immediately rotated back out of the main lumen before closing the tissue channel. The tissue channel is then closed and the tissue sample is retrieved, as described above, with cutting loop 138 outside of cannula 102. Cannula 102 is then rotated about axis 118, with cutting loop 138 energized, which causes cutting loop 138 to perform a first, planar, distal cut for a tissue sample from tissue adjacent to where the prior tissue sample had been taken. Second and third cuts are then performed in a manner similar to "one-stroke" process described above, except that cutting loop 138 is immediately rotated out of main lumen 122 after making the third, planar, proximal cut. Thus, several steps are eliminated from the "one-stroke" process, including opening and closing the tissue channel, which can lead to greater efficiency in the process.

Figure 15:
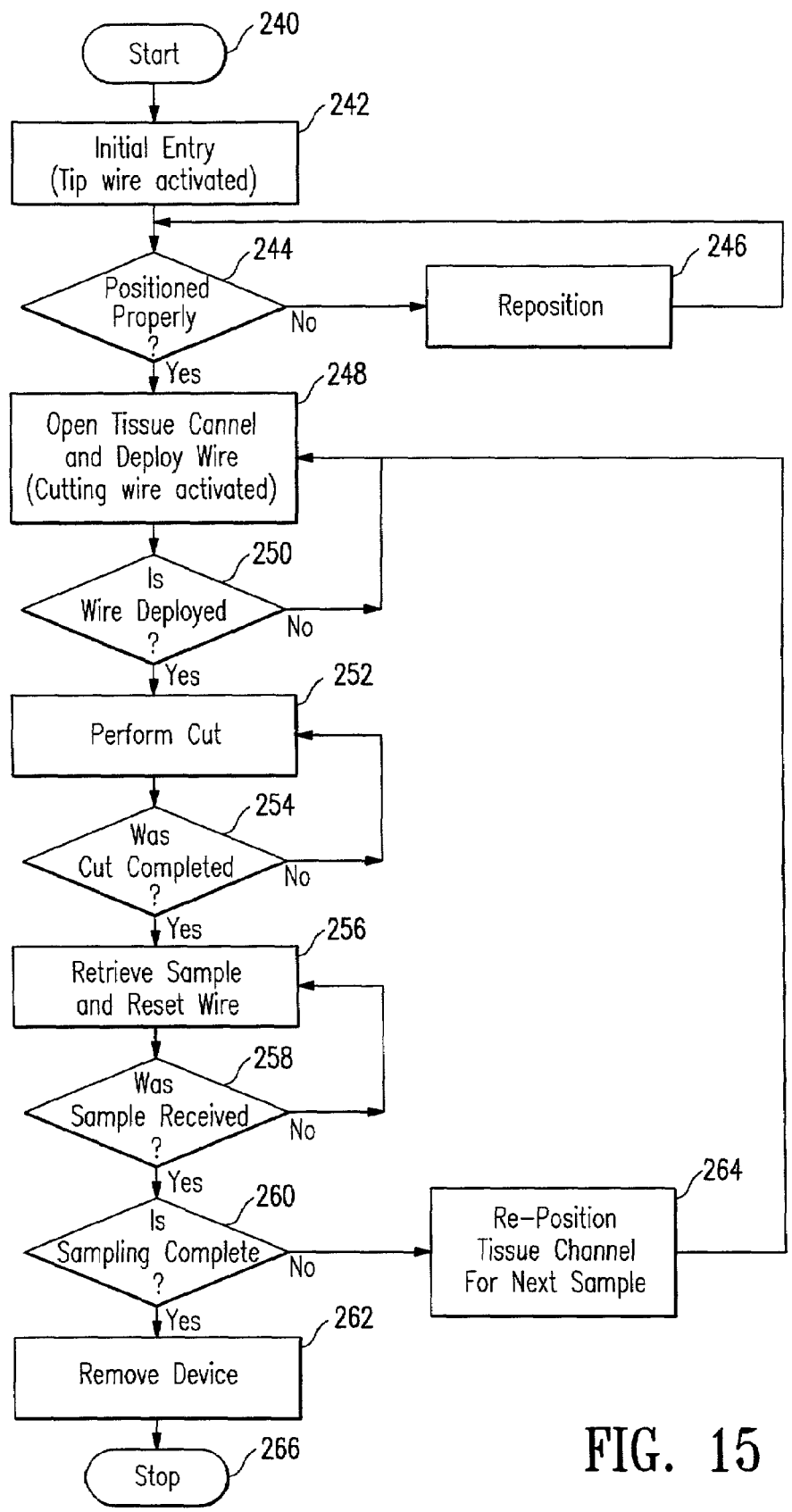
FIG. 15 is an illustration of an exemplary process.

FIG. 15 illustrates a flow diagram of the "two-stroke" process, described above with reference to Table 1. The logic contained in the process described in FIG. 15 can be implemented in controlling vacuum source 108, motor driver 112, and RF generator 106 by a programmable logic controller (not illustrated), a general purpose digital computer in communication with a memory element containing computer readable instructions which embody the control logic (not illustrated), application specific integrated circuit (ASIC) (not illustrated), or discrete digital signal processing (DDSP) (not illustrated).

At step 240, the process is initiated with patient preparation and equipment power-up sequences. At step 242, corresponding to step 1 in Table 1, cannula 102 is inserted into the tissue to be sampled. A decision is made at step 244 whether or not cannula 102 is properly positioned: if it is not, the cannula is repositioned at step 246, and step 244 is performed again. If cannula 102 is properly positioned, the "door" or tissue channel is opened, step 2 in Table 1, and cutting loop 138 is deployed, step 3 in Table 1. A decision is made whether cutting loop 138 is deployed: if not, step 248 is repeated. If cutting loop 138 is deployed, a longitudinal cut is performed at step 252, corresponding to step 5 in Table 1. A decision is then made whether the cut was completed: if not, step 252 is repeated; if the cut was completed, step 256 is performed. Step 256 corresponds to steps 6-9 in Table 1. After the wire has been reset in step 256, a decision is made at step 258 whether the sample has been received: if not, step 256 is repeated until the sample has been properly received. A decision is then made at step 260 whether sampling is complete: if not, the inner and outer cannulae are rotated relative to one another to close the "door" or tissue channel at step 264, and the process returns to step 248. If tissue sampling is complete, cannula 102 is removed from the patient in step 262, and post-procedure bandaging and tissue retrieval from tissue collector 114 is performed.

Figure 16:
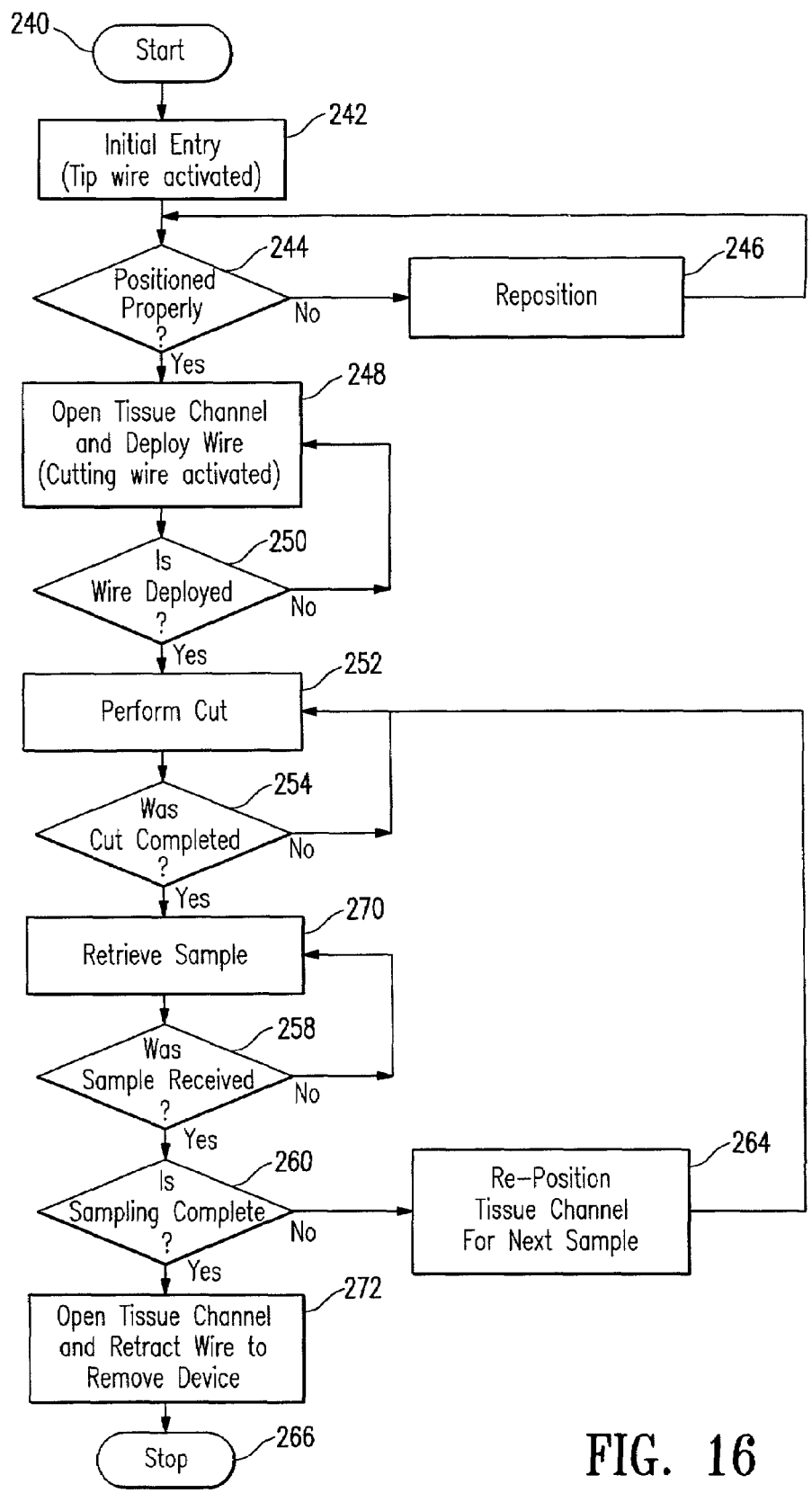
FIG. 16 is an illustration of an alternate process.

FIG. 16 illustrates a flow diagram of the "one-stroke" process, described above with reference to Table 2. Several of the steps of the process described in FIG. 16 are the same as those in the process described with reference to FIG. 15 and Table 1, and therefore will not be further described. The logic contained in the process described in FIG. 16 can be implemented in controlling vacuum source 108, motor driver 112, and RF generator 106 by a programmable logic controller (not illustrated), a general purpose digital computer in communication with a memory element containing computer readable instructions which embody the control logic (not illustrated), application specific integrated circuit (ASIC) (not illustrated), or discrete digital signal processing (DDSP) (not illustrated).

In FIG. 16, after the decision in step 254 is made that a complete longitudinal cut has been made, the sample is retrieved, as described above with reference to Table 2. After performing steps 258, and if the decision is made that sampling is not complete, step 264 is performed, and step 252 is repeated. As described above with reference to Table 2, the cut performed in step 252 is a longitudinal cut after cannula 102 has been rotated into a new volume of tissue. If sampling is complete after step 260, step 272 is performed, in which the status of the tissue channel or "door" is verified to be open, cutting loop 138 is rotated back into main lumen 122, and cannula 102 is removed from the patient.

Figure 17:
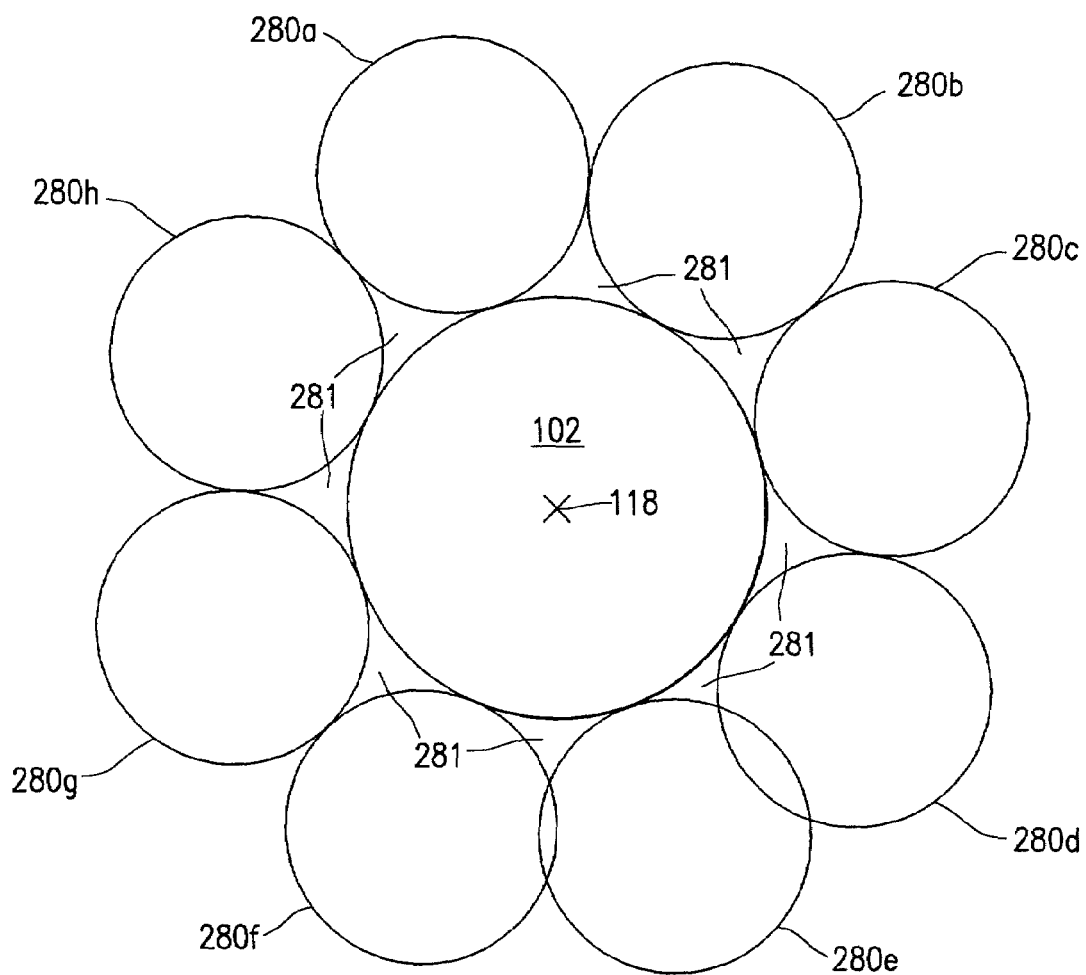
FIG. 17 is an illustration of cuts that can be made in tissue.
Figure 18:
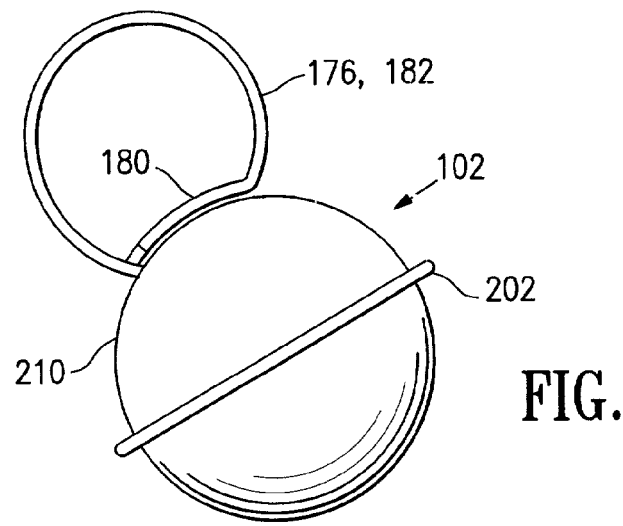
FIG. 18 is an end view of yet another exemplary embodiment of a cannula.
Figure 19:
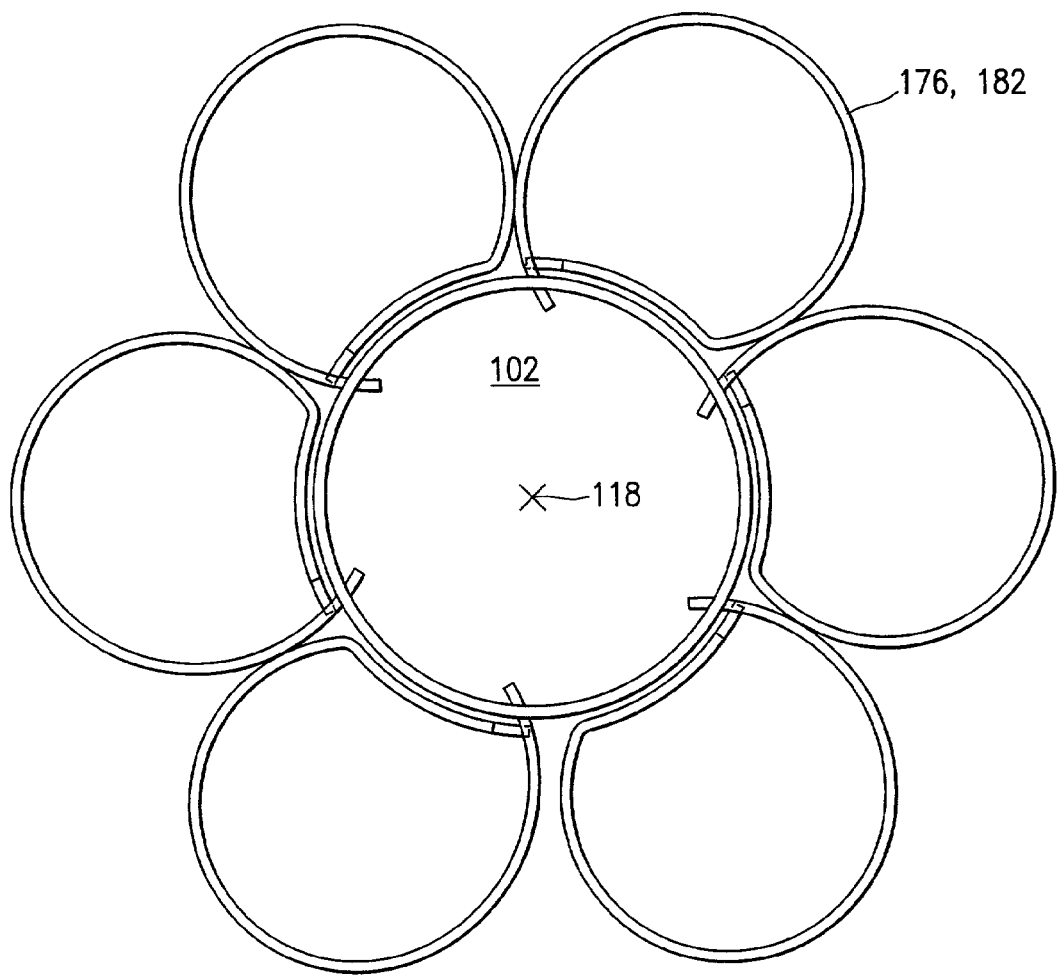
FIG. 19 is an illustration of cuts that can be made in tissue.

FIG. 17 illustrates a cutting pattern achieved by a system 100. In FIG. 17, a plurality of cylindrical cuts 280a-h are made by cannula 102 having a cutting loop 138 (not illustrated in FIG. 17). As illustrated in FIG. 17, while system 100 retrieves a plurality of samples, small areas 281 are left unsampled, because cutting loop 138 is generally circular. Cutting loops 176, 182, and 186 are specifically configured to extend cylindrical cuts 280 into these areas. For example, FIG. 18 illustrates a distal end view of cannula 102 including cutting loop 176 or 182, which includes portion 180 which closely conforms to the external diameter of cannula 102. Thus, cutting loop 176 or 182 extends into areas 281 when longitudinal cuts are performed, which samples tissue closer to the center of the tissue mass of interest, as illustrated in FIG. 19. Alternatively, cannula 102 can merely be rotated around axis 118 less, which overlaps the cutting cylinders more in each cutting stroke, thus reducing the volume of unsampled tissue.

Yet another embodiment of a cutting wire is illustrated in FIGS. 20 and 21. FIG. 20 illustrates a bipolar cutting wire 300 which includes a simple cutting loop 302 and an actuating portion 304 which extends proximally from cutting loop 302. Cutting wire 300 is a bipolar cutting wire and includes two conductors therein of approximately equal surface area. Cutting loop 302 includes a first, inner loop 306, an insulating layer 308, and an outer loop 310. Inner and outer cutting loops 306, 310 are formed of materials similar to those of the cutting loops previously described, while insulating layer 308 is formed of a material which electrically insulates cutting loops 306, 310 from each other when energized. As illustrated in FIG. 21, which illustrates a cross-sectional view of cutting loop 302 taken at line 21-21 in FIG. 20, each of inner and outer cutting loops 306, 310 are connected physically and electrically to conductors 312, 314, respectively, which are part of or comprise actuating portion 304. An insulating and/or reinforcing layer 316 may be provided between conductors 312, 314, to electrically insulate the conductors from each other, and to add mechanical strength to actuating portion 304.

According to yet another embodiment, illustrated schematically in FIG. 1 with dotted line 320 and in greater detail in FIG. 22, patient return pad 110 is replaced in system 100 with a return electrode 322 that is formed into cannula 152, thus making cannula 102 a pseudo-bipolar RF cutting device. Cannula 102 is not a true bipolar cutting device in this embodiment, because a true bipolar device includes electrodes with substantially the same surface area, while return electrode 322 has a surface area significantly greater than the cutting loop. A large portion of the distal end of outer cannula 152 is the return electrode for the RF circuit, except for small portions at sidewalls 164, 166 and endwalls 168 and 170. Sidewalls 164, 166 and endwalls 168 and 170 are preferably formed to be electrically insulating, so that incidental contact between the cutting loop and the sidewall will not short the RF energy circuit. Sidewalls 164, 166 and endwalls 168 and 170 can be coated with an electrically insulating material, formed of a different material and integrated into outer cannula 152, or may comprise any other suitable structure which electrically insulates the cutting loop from the outer cannula. Outer cannula 152 includes an electrical conductor 324 connected between return electrode 322 and RF generator 106.

According to yet another embodiment (not illustrated), the device or mechanism by which the tissue samples are retrieved is not limited to only a source of vacuum. Instead of or in addition to vacuum source 108, a tissue sampling mechanism can further include a grasper that is extendable through main lumen 122 to grasp a tissue sample therein and allow the practitioner to pull the sample proximally out of the cannulae. Alternatively, a tissue sampling mechanism can further include a piston-like element in the distal portions of main lumen 122, which can be caused to move proximally in main lumen 122 to push a tissue sample therein proximally out of the cannulae. Other embodiments of tissue sampling mechanisms will be readily apparent to one of ordinary skill in the art and within the spirit and scope of the invention.

While the invention has been described in detail with reference to preferred embodiments thereof, it will be apparent to one skilled in the art that various changes can be made, and equivalents employed, without departing from the scope of the invention.

The invention claimed is:

1. A tissue acquisition device useful in retrieving tissue samples from a patient, comprising:
   an inner cannula having a proximal end, a distal end, a longitudinal axis extending between said proximal and distal ends, a tubular sidewall, a cut out in the sidewall proximal to the distal end and a first inner lumen extending within at least a portion of the inner cannula to the cut out in the sidewall;
   an outer cannula having a proximal end, a distal end, a longitudinal axis extending between said proximal and distal ends, a tubular sidewall, a cut out in the tubular sidewall of the outer cannula proximal to the distal end and a second inner lumen extending within at least a portion of the outer cannula;
   a tissue penetrating distal tip; and
   an electrically conducting cutting wire slidably and rotatably disposed in the first inner lumen of the inner cannula, having a proximal end and a distal end and having a cutting loop at a said distal end which is configured to rotate from a position within the inner cannula out of the inner cannula through the cut out in the side wall thereof in a plane traversing the longitudinal axes of the inner and outer cannulas to a position exterior to the outer cannula, to move longitudinally in a direction generally parallel to the longitudinal axes exterior to the outer cannula and to rotate from a position exterior to the outer cannula into the inner cannula through the cut outs in the side wall of the inner and outer cannulas in a plane traversing the longitudinal axes.

2. The tissue acquisition device of claim 1, wherein said electrically conducting cutting wire is configured to make electrical contact with a source of radio-frequency electrical energy.

3. The tissue acquisition device of claim 1, wherein said cutting loop is a RF energy cutting loop.

4. The tissue acquisition device of claim 1, wherein said cutting loop comprises a material selected from the group consisting of stainless steel, tungsten, platinum, and nickel-titanium alloy.

5. The tissue acquisition device of claim 1 including a vacuum source in fluid communication with the main lumen of the inner cannula to draw a tissue specimen into the inner cannula through the cut outs of the inner and outer cannulas.

6. The tissue acquisition device of claim 1, further comprising an end plug disposed on the distal end of said device.

7. The tissue acquisition device of claim 6, further comprising an electrically conducting distal cutting wire disposed distal to said end plug.

8. The tissue acquisition device of claim 1, further comprising an electrically conducting distal cutting wire disposed near the distal end of said device.

9. The tissue acquisition device of claim 8, wherein said electrically conducting distal cutting wire is configured to make electrical contact with a source of radio-frequency electrical energy.

10. The tissue acquisition device of claim 9, wherein said electrically conducting distal cutting wire comprises a material selected from the group consisting of stainless steel, tungsten, platinum, and nickel-titanium alloy.

11. A tissue acquisition device useful in retrieving tissue samples from a patient, comprising:
an elongated probe member having a tubular member with a proximal end, a distal end, a tissue penetrating distal tip at the distal end, a longitudinal axis extending between said proximal and distal ends, a cut out in a wall of the tubular member proximal to the distal end, a first inner lumen extending within at least a portion of the tubular member to and in fluid communication with the cut out in the wall of the tubular member and a second inner lumen extending within the wall of the tubular member proximal to the cut out therein; and
an electrically conducting cutting wire which is slidably and rotatably disposed in the second inner lumen, which has a distal end and a cutting loop at the distal end which is configured to rotate from a first position within the tubular member out of the cut out in the tubular member in a plane traversing the longitudinal axis to a second position exterior to the tubular member, to move longitudinally in a direction generally parallel to the longitudinal axis in the second position and exterior to the elongated tubular member and to rotate from the second position exterior to the elongated tubular member into the elongated tubular member through the cut out in the tubular member in a plane traversing the longitudinal axis so as to sever a cylindrical tissue sample from surrounding tissue while subjected to high frequency electrical power.

12. The tissue acquisition device of claim 11, wherein said electrically conducting cutting wire is configured to be electrically connected to a source of radio-frequency electrical energy.

13. The tissue acquisition device of claim 11, wherein the cutting loop is formed at least in part of a material selected from the group consisting of stainless steel, tungsten, platinum, and nickel-titanium alloy.

14. The tissue acquisition device of claim 11, wherein an electrically conducting distal cutting wire extends over the tissue penetrating distal tip to facilitate passage through tissue when the distal cutting wire is subjected to electrical power.

15. The tissue acquisition device of claim 11 including a vacuum source in fluid communication with the inner lumen of the probe member to draw a tissue specimen into the inner lumen through the cut out of the probe member.

* * * * *